(12) United States Patent
Gupta et al.

(10) Patent No.: US 6,355,708 B2
(45) Date of Patent: Mar. 12, 2002

(54) TRISARYL-1,3,5-TRIAZINE ULTRAVIOLET LIGHT ABSORBERS

(75) Inventors: Ram Baboo Gupta, Stamford; Dennis John Jakiela, Orange; Gottfried Haacke, New Canaan, all of CT (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/832,613

(22) Filed: Apr. 11, 2001

Related U.S. Application Data

(62) Division of application No. 09/195,830, filed on Nov. 19, 1998, now Pat. No. 6,242,597.
(60) Provisional application No. 60/066,358, filed on Nov. 21, 1997.

(51) Int. Cl.$^7$ .................. C08K 5/3492; C09K 15/22
(52) U.S. Cl. .................. 524/100; 252/403; 524/94; 528/423
(58) Field of Search .................. 252/403; 524/94, 524/100; 528/423

(56) References Cited

U.S. PATENT DOCUMENTS

| | | | |
|---|---|---|---|
| 5,354,794 A | 10/1994 | Stevenson et al. | 524/100 |
| 5,476,937 A | 12/1995 | Stevenson et al. | 544/216 |
| 5,543,518 A | 8/1996 | Stevenson et al. | 544/215 |
| 5,556,973 A | 9/1996 | Stevenson et al. | 544/216 |
| 5,597,854 A | 1/1997 | Birbaum et al. | 544/216 |

FOREIGN PATENT DOCUMENTS

| | | |
|---|---|---|
| WO | 96/28431 | 9/1996 |

*Primary Examiner*—Kriellion A. Sanders
(74) *Attorney, Agent, or Firm*—Tyler A. Stevenson

(57) ABSTRACT

The present invention relates to novel bondable trisaryl-1,3,5-triazines containing active (acidic) hydrocarbons and the use thereof as an ultraviolet light absorber. The presently claimed compounds are particularly useful, either alone or in combination with other additives, including other ultraviolet light absorbers and stabilizers, in stabilizing polymers and other materials from degradation by environmental forces such as actinic radiation (ultraviolet light), oxidation, moisture, atmospheric pollutants and combinations thereof.

10 Claims, No Drawings

TRISARYL-1,3,5-TRIAZINE ULTRAVIOLET LIGHT ABSORBERS

This application claims the benefit under 35 USC 119 of U.S. provisional application No. 60/066,358, filed Nov. 21, 1997 and is a divisional of application Ser. No. 09/195,830, filed Nov. 19, 1998 now U.S. Pat. No. 6,242,597.

BACKGROUND OF THE INVENTION

1. Field of the Invention

This invention relates generally to novel trisaryl-1,3,5-triazine compounds containing active (acidic) hydrogen atoms and the use thereof to protect against degradation by environmental forces, inclusive of actinic radiation (such as ultraviolet light), oxidation, moisture, atmospheric pollutants and combinations thereof.

2. Description of Related Art

Exposure to sunlight and other sources of ultraviolet radiation is known to cause degradation of a variety of materials, especially polymeric materials. For example, polymeric materials such as plastics often discolor and/or become brittle as a result of prolonged exposure to ultraviolet light. Accordingly, a large body of art has been developed directed towards materials such as ultraviolet light absorbers and stabilizers which are capable of inhibiting such degradation.

A class of materials known to be ultraviolet light absorbers are trisaryl-1,3,5-triazines, in which at least one of the aryl rings has a hydroxyl group ortho to the point of attachment to the triazine ring. In general this class of materials is well known in the art. Disclosures of a number of such trisaryl-1,3,5-trazines, as well as processes for preparing and uses thereof, can be found in the following publications, all of which are incorporated by reference herein for all purposes as if fully set forth: U.S. Pat. No. 3,118,887, U.S. Pat. No. 3,242,175, U.S. Pat. No. 3,244,708, U.S. Pat. No. 3,249,608, U.S. Pat. No. 3,268,474, U.S. Pat. No. 3,423,360, U.S. Pat. No. 3,444,164, U.S. Pat. No. 3,843,371, U.S. Pat. No. 4,619,956, U.S. Pat. No. 4,740,542, U.S. Pat. No. 4,775,707, U.S. Pat. No. 4,826,978, U.S. Pat. No. 4,831,068, U.S. Pat. No. 4,962,142, U.S. Pat. No. 5,030,731, U.S. Pat. No. 5,059,647, U.S. Pat. No. 5,071,981, U.S. Pat. No. 5,084,570, U.S. Pat. No. 5,106,891, U.S. Pat. No. 5,185,445, U.S. Pat. No. 5,189,084, U.S. Pat. No. 5,198,498, U.S. Pat. No. 5,288,778, U.S. Pat. No. 5,298,067, U.S. Pat. No. 5,300,414, U.S. Pat. No. 5,322,868, U.S. Pat. No. 5,354,794, U.S. Pat. No. 5,364,749, U.S. Pat. No. 5,369,140, U.S. Pat. No. 5,410,048, U.S. Pat. No. 5,412,008, U.S. Pat. No. 5,420,204, U.S. Pat. No. 5,461,151, U.S. Pat. No. 5,476,937, U.S. Pat. No. 5,478,935, U.S. Pat. No. 5,489,503, U.S. Pat. No. 5,543,518, U.S. Pat. No. 5,538,840, U.S. Pat. No. 5,545,836, U.S. Pat. No. 5,563,224, U.S. Pat. No. 5,575,958, U.S. Pat. No. 5,591,850, U.S. Pat. No. 5,597,854, GB1033387, CH480091, CH484695, EP-A-0434608, EP-A-0444323, EP-A-0532006, EP-A-0649841, EP-A-0693483, EP-A-0704560, WO94/05645, WO95/22959 and WO96/28431.

Typically, the aforementioned aryl ring with the hydroxyl group ortho to the point of attachment to the triazine ring is based on resorcinol and, consequently, this aryl ring also contains a second substituent (either a hydroxyl group or a derivative thereof) para- to the point of attachment to the triazine ring. This second substituent can be "non-reactive," as in the case of an alkyloxy group, or "reactive," as in the case of a hydroxyalkyloxy (active hydrogen reactive site) or (meth)acryloyl (ethylenic unsaturation reactive site) group.

For the purposes of the present invention, the former are referred to as "non-bondable" trisaryl-1,3,5-triazines and the latter are referred to as "bondable" trisaryl-1,3,5-triazines.

Many polymer additives (such as ultraviolet light stabilizers) may suffer from a disadvantage that they volatilize or migrate out of the polymer substrate to be protected, or that they are adsorbed (chemically or physically) by one or more systems components (such as pigments), thereby diminishing their effectiveness.

Bondable stabilizers have a potential advantage in this respect in that, depending on the bondable functionality and the particular polymer system to be stabilized, they can be chemically incorporated into a polymer structure via reaction of the bondable functionality either during polymer formation (such as in the case of polymerizing monomers or a crosslinking polymer system) or subsequently with a preformed polymer having appropriate reactive functionality. Accordingly, due to such bonding, migration of these UV absorbers between layers of multi-layer coatings and into polymer substrates and between coatings and their plastic substrates is greatly reduced.

Several of the previously incorporated references disclose bondable trisaryl-1,3,5-triazines. For example, previously incorporated U.S. Pat. No. 3,423,360, U.S. Pat. No. 4,962,142 and U.S. Pat. No. 5,189,084 disclose various bondable trisaryl-1,3,5-triazines and the incorporation of these compounds into polymers by chemical bonding. However, the inventors are unaware of any prior art which discloses the novel functionalized trisaryl-1,3,5-triazines of the present invention.

SUMMARY OF THE INVENTION

The present invention provides a new class of bondable trisaryl-1,3,5-triazines in which an aryl ring attached to the triazine ring (and preferably an aryl ring containing a hydroxyl group or "latent" hydroxyl group ortho- to the point of attachment to the triazine ring) is substituted with a bondable group, containing one or more active (acidic) hydrogen containing groups para- to the point of attachment to the triazine ring. As examples of such active (acidic) hydrogen containing groups may be mentioned 1,3-dicarbonyls, 1,3-diketones, 1,3-diesters (malonate esters), 1,3-ketoesters, beta-carbonyl cyano compounds, 1,3-sulfur compounds, 1,3-disulfones and 1,3-disulfoxides.

More specifically, the new trisaryl-1,3,5-triazines of the present invention have the following general formulas (I), (II) and (III):

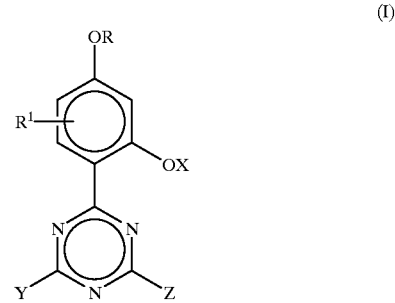

(I)

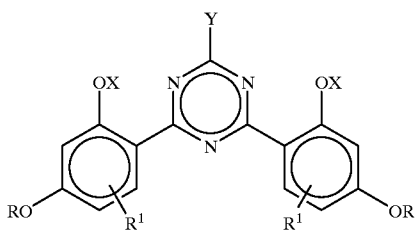

(II)

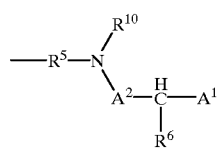

(VI)

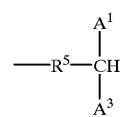

(VII)

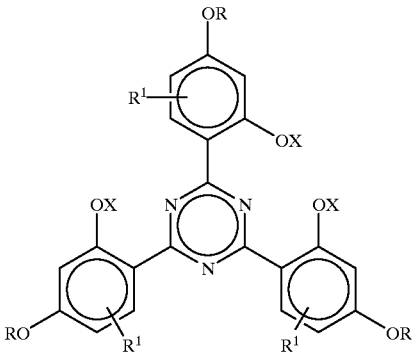

(III)

wherein each X is independently selected from hydrogen and a blocking group; each of Y and Z is independently selected from an aryl ring of the general formula (IV)

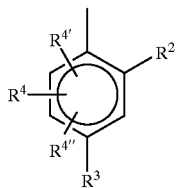

(IV)

each R is independently selected from a hydrogen, a hydrocarbyl group and a functional hydrocarbyl group;

each $R^1$, $R^2$, $R^4$, $R^{4''}$ and $R^{4'''}$ is independently selected from hydrogen, hydrocarbyl, functional hydrocarbyl, —O(hydrocarbyl), —O(functional hydrocarbyl), —SR, halogen, —$SO_2R$, —$SO_3R$, —COOR, —COR, —OCOR, —NRR and cyano; and each $R^3$ is independently selected from —R, —OR, —SR, halogen, —$SO_2R$, —$SO_3R$, —COOR, —COR, —NRR and cyano;

characterized in that at least one R group of a 4-position —OR group is selected from a group of the general formulas (V), (VI) and (VII):

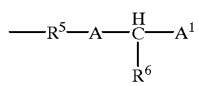

(V)

wherein

A is selected from —O(O)C—; —C(O)—; —SO—; —$SO_2$—; and —$OSO_2$—;

each of $A^1$ and $A^3$ is independently selected from —$COOR^7$; —COO$^-$M$^+$; —C(O)$R^7$; —C(O)NR$^7$R$^8$; —CN; —$NO_2$; —$SO_2R^7$; —$SO_2OR^7$; —$SO_2OR^7$ and —$SO_2NR^7R^8$;

$A^2$ is selected from —C(O)—; —$R^9$C(O)—; —$R^9$OC(O)—; —SO—; $R^9$SO—; —$SO_2$; —$R^9SO_2$—; and —$R^9OSO_2$—;

$M^+$ is a cationic moiety;

each of $R^5$ and $R^9$ is independently a hydrocarbylene group;

$R^6$ is selected from H and an alkyl of 1–4 carbon atoms; and each of $R^7$, $R^8$ and $R^{10}$ is independently selected from H, a hydrocarbyl group and a functional hydrocarbyl group.

These tris-aryl-1,3,5-triazines of the present invention have the added benefit of being capable of chemically bonding to appropriate polymer systems via the acidic active hydrogen. Since, in the above formulas, the acidic active hydrogen is from an active methylene or methine group, the further advantage of very stable carbon-carbon bonding is possible.

These trisaryl-1,3,5-triazines may in general be prepared via a number of procedures, but preferably by reacting a trisaryl-1,3,5-triazine precursor, having at least one aryl ring with an amino, amido and/or hydroxyl group containing —OR moiety para to the point of attachment to the triazine ring (and preferably also a hydroxyl group ortho to the point of attachment to the triazine ring), with an appropriate compound or compounds to functionalize the para position —OR group with a group of the above formula (V) and/or (VI). Further preferred process details are disclosed below.

The novel trisaryl-1,3,5-triazines of the present invention are particularly useful as ultraviolet light absorber agents for stabilizing a wide variety of materials including, for example, organic compounds, oils, fats, waxes, cosmetics, dyes and biocides, and particularly various organic polymers (both crosslinked and non-crosslinked) used in applications such as photographic materials, plastics, rubbers, paints and other coatings, and adhesives, such as disclosed in a number of the previously incorporated references. The present invention, consequently, also relates to (1) a method of stabilizing a material which is subject to degradation by actinic radiation (e.g., an organic material such as an organic polymer in the form of a film, fiber or shaped article) by incorporating into said material an amount of an actinic radiation stabilizer composition effective to stabilize the material against the effects of actinic radiation, wherein the actinic radiation stabilizer composition comprises the inventive trisaryl-1,3,5-triazines; and (2) the material so stabilized.

The novel trisaryl-1,3,5-triazines of the present invention are also effective as ultraviolet light screening agents in applications such as sunscreens and other cosmetic preparations, capstock layers for extruded polymers, dyed fibers and laminated UVscreening window films, among others. The present invention, consequently, also relates (1) to a method of protecting a substrate against degradation by actinic radiation by applying to the substrate an actinic radiation screening layer (e.g., a coating film or capstock layer) containing an actinic radiation screening composition in an amount effective to reduce the amount of actinic radiation impinging on the substrate, wherein the actinic radiation screening composition comprises the inventive trisaryl-1,3,5-triazines: and (2) the substrate so protected, e.g., the actinic screening layer plus the substrate so protected.

The novel trisaryl-1,3,5-triazines of the present invention may also be employed to form light stabilizing compositions. Such light stabilizing compositions may include a variety of other components known in the art including other ultraviolet absorbers and stabilizers, antioxidants and the like.

These and other features and advantages of the present invention will be more readily understood by those of ordinary skill in the art from a reading of the following detailed description.

DETAILED DESCRIPTION OF THE PREFERRED EMBODIMENTS

The Novel Trisaryl-1,3,5-Triazines

As indicated above, the trisaryl-1,3,5-triazines in accordance with the present invention are compounds of the general formulas (I), (II) and (III).

The term "hydrocarbyl" in the context of the present invention, and in the above formulas, broadly refers to a monovalent hydrocarbon group in which the valency is derived by abstraction of a hydrogen from a carbon atom. Hydrocarbyl includes, for example, aliphatics (straight and branched chain), cycloaliphatics, aromatics and mixed character groups (e.g., aralkyl and alkaryl). Hydrocarbyl also includes such groups with internal unsaturation and activated unsaturation. More specifically, hydrocarbyl includes (but is not limited to) such groups as alkyl, cycloalkyl, aryl, aralkyl, alkaryl, alkenyl, cycloalkenyl and alkynyl, preferably having up to 24 carbon atoms. A hydrocarbyl may optionally contain a carbonyl group or groups (which is/are included in the carbon count) and/or a heteroatom or heteroatoms (such as at least one oxygen, sulfur, nitrogen or silicon), in the chain or ring.

The term "functional hydrocarbyl" in the context of the present invention, and in the above formulas, broadly refers to a hydrocarbyl possessing pendant and/or terminal reactive" and/or "latent reactive" functionality and/or leaving groups. Reactive functionality refers to functionality which is reactive with common monomer/polymer functionality under normal conditions well understood by those persons of ordinary skill in the relevant art. As examples of reactive functionality may be mentioned active hydrogen containing groups such as hydroxyl, amino, carboxyl, thio, amido, carbamoyl and activated methylene; isocyanato cyano; epoxy; ethylenically unsaturated groups such as allyl and methallyl; and activated unsaturated groups such acryloyl and methacryloyl, and maleate and maleimido (including the Diels-Alder adducts thereof with dienes such as butadiene). Latent reactive functionality within the meaning of the present invention and, as would clearly be understood by those persons of ordinary skill in the relevant art, refers to reactive functionality which is blocked or masked to prevent premature reaction. As examples of latent reactive functionality may be mentioned ketimines and aldimines (amines blocked, respectively, with ketones and aldehydes); aminecarboxylate salts; and blocked isocyanates such as alcohol (carbamates), oxime and caprolactam blocked variations. A "leaving" group within the meaning of the present invention and, as would clearly be understood by those persons of ordinary skill in the relevant art, is a substituent attached to the hydrocarbyl chain or ring which during reaction is displaced to create a valency on a carbon or hetero atom in the hydrocarbyl chain or ring. As examples of leaving groups may be mentioned halogen atoms such as chlorine, bromine and iodine; hydroxyl groups; quaternary ammonium salts ($NT_4^+$); sulfonium salts ($ST_3^+$); and sulfonates ($-OSO_3T$); where T is, e.g., methyl or para-tolyl. Preferred functionality includes hydroxyl, $-COOR^{11}$, $-CR^{12}=CH_2$, $-CO-CR^{12}=CH_2$, $-OCO-CR^{12}=CH_2$, $-OCO-NH-R^8$, Cl,

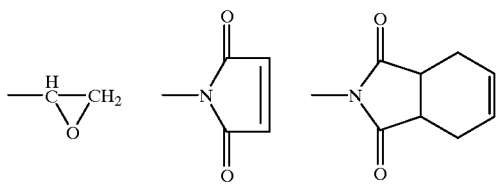

an isocyanate group, a blocked isocyanate group and $-NHR^{11}$, wherein $R^{11}$ is selected from hydrogen and a hydrocarbyl (preferably of up to 24 carbon atoms); and $R^{12}$ is selected from hydrogen and an alkyl of 1 to 4 carbon atoms (preferably hydrogen and methyl).

The term "hydrocarbylene" in the context of the present invention is a divalent hydrocarbon group in which both valencies derive by abstraction of hydrogens from carbon atoms. Included within the definition of hydrocarbylene are the same groups as indicated above for hydrocarbyl and functional hydrocarbyl with, of course, the extra valency (for example, alkylene, alkenylene, arylene, alkylarylene, etc.).

The term "functional hydrocarbylene" in the context of the present invention refers to a species of hydrocarbylene possessing pendant reactive functionality, latent reactive functionality and/or leaving groups. The term "nonfunctional hydrocarbylene" in the context of the present invention refers generally to a hydrocarbylene other than a functional hydrocarbylene.

The trisaryl-1,3,5-triazines in accordance with the present invention also relate to latent stabilizing compounds against actinic radiation of the general formulas (I), (II) and (III), wherein at least one of the hydroxyl groups on an aryl ring ortho to the point of attachment to the triazine ring is blocked, that is, wherein at least one X is other than hydrogen. Such latent stabilizing compounds liberate the effective stabilizers by cleavage of the O—X bond, e.g., by heating or by exposure to UV radiation. Latent stabilizing compounds are desirable because they have many favorable properties, i.e., good substrate compatibility, good color properties, a high conversion rate of the O—X group to an OH group, and a long shelf life. The use of latent stabilizing compounds is further described in U.S. Pat. No. 4,775,707, U.S. Pat. No. 5,030,731, U.S. Pat. No. 5,563,224 and U.S. Pat. No. 5,597,854, which are incorporated herein for all purposes as if fully set forth.

Latent stabilizing compounds comprising the trisaryl-1, 3,5-triazines in accordance with the present invention can be prepared from compounds of the general formulas (I), (II) and (III) wherein at least one X is hydrogen by subjecting said compounds to a further reaction to form latent stabilizing compounds, as described in the immediately preceding incorporated references.

As preferred examples of blocking groups X may be mentioned one or more of the following groups: allyl, —$COR^a$, —$SO_2R^b$, —$SiR^cR^dR^e$, —$PR^fR^g$ or —$POR^fR^g$, —$CONHR^h$,
wherein each $R^a$ is independently selected from $C_1$-$C_8$ alkyl, halogen-substituted $C_1$-$C_8$ alkyl, $C_5$-$C_{12}$ cycloalkyl, $C_2$-$C_8$ alkenyl, —$CH_2$—CO—$CH_3$, $C_1$-$C_{12}$ alkoxy, and phenyl or phenoxy which is unsubstituted or substituted by $C_1$-$C_{12}$ alkyl, $C_1$-$C_4$ alkoxy, halogen and/or benzyl;

each $R^b$ is independently selected from $C_1$-$C_{12}$ alkyl, $C_6$-$C_{10}$ aryl and $C_7$-$C_{18}$ alkylaryl;

each $R^c$, $R^d$ and $R^e$ is independently selected from $C_1$-$C_{18}$, alkyl, cyclohexyl, phenyl and $C_1$-$C_{18}$ alkoxy;

each $R^f$ and $R^g$ is independently selected from $C_1$-$C_{12}$ alkoxy, $C_1$-$C_{12}$ alkyl, $C_5$-$C_{12}$ cycloalkyl, and phenyl or phenoxy which is unsubstituted or substituted by $C_1$-$C_{12}$ alkyl, $C_1$-$C_4$ alkoxy, halogen and/or benzyl; and each $R^h$ is independently selected from $C_1$-$C_8$ alkyl, $C_5$-$C_{12}$ cycloalkyl, $C_2$-$C_8$ alkenyl, —$CH_2$—CO—$CH_3$, and phenyl which is unsubstituted or substituted by $C_1$-$C_{12}$ alkyl, $C_2$-$C_8$ alkenyl, $C_1$-$C_4$ alkoxy, halogen and/or benzyl.

The reaction to give the latent stabilizing compounds of the present invention of the general formulas (I), (II) and (III) in which X is allyl, —$COR^a$, —$SO_2R^b$, —$SiR^cR^dR^e$, —$PR^fR^g$ or —$POR^fR^g$ can be carried out, for example, by reaction of the compounds of the general formulas (I), (II) and (III) wherein at least one X is hydrogen with the corresponding halides such as allyl chloride, Cl—$COR^a$, Cl—$SO_2R^b$, Cl—$SiR^cR^dR^e$, Cl—$PR^fR^g$, or Cl—$POR^fR^g$. The reaction to give the latent stabilizing compounds of the present invention of the general formulas (I), (II) and (III) in which X is —$CONHR^h$ can be carried out, for example, by reaction of the compounds of the general formulas (I), (II) and (III) wherein at least one X is hydrogen with the corresponding isocyanates. Furthermore, acylated compounds can be obtained by reaction with anhydrides, ketenes or esters, such as lower alkyl esters, as is well known to one skilled in the art. The above-described reagents may be used in approximately equimolar amounts or in excess, for example, from 2 to 20 mol with respect to the hydroxyl groups desired to be made latent in the starting compound of the general formula (I), (II) or (III).

Catalysts customarily used for acylation, sulfonylation, phosphonylation, silylation or urethanation reactions may be used in forming the latent stabilizing trisaryl-1,3,5-triazines of the present invention. For example, acylation and sulfonylation reaction catalysts such as tertiary or quaternary amines, such as triethylamine, dimethylaminopyridine or tetrabutylammonium salts, may be used for forming these latent stabilizing compounds.

The reaction may be carried out in the presence of a solvent, such as relatively inert organics, e.g., hydrocarbons such as toluene and xylene, chlorinated hydrocarbons such as carbon tetrachloride or chloroform, or ethers such as tetrahydrofuran or dibutyl ether, or without a solvent. Alternatively, the reagent(s) may be employed as the solvent. The reaction temperature is usually between room temperature and about 150° C., for example, up to the boiling point of the solvent when a solvent is used.

In preferred embodiments, each X is hydrogen.

In preferred embodiments, those R groups which are not either a group of the formula (V), (VI) or (VII) are independently selected from hydrogen, a hydrocarbyl group of 1 to 50 carbon atoms; and a functional hydrocarbyl group of 1 to 50 carbon atoms. More preferably, each such R group is independently selected from hydrogen, an alkyl of 1 to 24 carbon atoms (which may optionally be substituted by one or more hydroxyl, carboxyl, carboalkoxy (ester), amide, epoxy and/or amino groups and/or contain one or more carbonyl groups, oxygen atoms and/or nitrogen atoms in the chain); an alkenyl of 2 to 24 carbon atoms (which may optionally be substituted by hydroxyl, carboxyl, epoxy and/or amino group(s) and/or contain carbonyl, oxygen and/or nitrogen in the chain), a cycloalkyl of 5 to 24 carbon atoms (which may optionally be substituted by hydroxyl, carboxyl and/or amino group(s) and/or contain carbonyl, oxygen and/or nitrogen in the ring), and an aralkyl of 7 to 24 carbon atoms (which may optionally be substituted by hydroxyl, carboxyl and/or amino group(s) and/or contain carbonyl, oxygen and/or nitrogen in the ring).

More preferably, each R group is independently selected from hydrogen, an alkyl of 1 to 24 carbon atoms optionally containing an oxygen atom in the chain, a hydroxyalkyl of 1 to 24 carbon atoms optionally containing an oxygen atom in the chain, a group of the formula (V), a group of the formula (VI) and a group of the formula (VII), with the proviso that at least one such R group is a group of the formula (V), (VI) or (VII).

In preferred embodiments, each $R^1$ is independently selected from hydrogen, halogen, an acyl of 2 to 12 carbon atoms, an acyloxy of 2 to 12 carbon atoms, a hydrocarbyl having from 1 to 24 carbon atoms and a functional hydrocarbyl having from 1 to 24 carbon atoms; more preferably from hydrogen, halogen, an alkyl of 1 to 24 carbon atoms, a functional alkyl of 1 to 24 carbon atoms, an alkenyl of 2 to 24 carbon atoms, a cycloalkyl of 5 to 12 carbon atoms; and especially hydrogen.

In preferred embodiments, each $R^2$ is independently selected from hydrogen, halogen, a hydrocarbyl group of 1 to 24 carbon atoms, a hydrocarbyloxy group of 1 to 24 carbon atoms, an acyl group of 2 to 24 carbon atoms and an acyloxy group of 2 to 24 carbon atoms. More preferably, each $R^2$ is independently selected from hydrogen; halogen; an alkyl of 1 to 24 carbon atoms optionally containing an oxygen atom in the chain; an alkyloxy of 1 to 24 carbon atoms optionally containing an oxygen atom in the chain; an alkenyl of 2 to 24 carbon atoms optionally containing an oxygen atom in the chain; an alkenyloxy of 2 to 24 carbon atoms optionally containing an oxygen atom in the chain; and an acyloxy group of 2 to 12 carbon atoms. Still more preferably, each $R^2$ is independently selected from hydrogen, an alkyl of 1 to 8 carbon atoms, an alkyloxy of 1 to 8 carbon atoms optionally containing an oxygen atom in the chain, a hydroxyalkyl of 1 to 8 carbon atoms optionally containing an oxygen atom in the chain, a hydroxyalkyloxy of 1 to 8 carbon atoms group optionally containing an oxygen atom in the chain, and an acyloxy of 2 to 12 carbon atoms. Especially preferred is when each $R^2$ is independently selected from hydrogen and an alkyl of 1 to 4 carbon atoms and particularly hydrogen and methyl.

In preferred embodiments, each $R^3$ is independently selected from hydrogen, halogen, a hydrocarbyl group of 1 to 24 carbon atoms, a functional hydrocarbyl group of 1 to 24 carbon atoms and —OR. More preferably, each $R^3$ is independently selected from hydrogen; an alkyl of 1 to 24 carbon atoms (which may optionally be substituted by hydroxyl, carboxyl and/or amino group(s) and/or contain carbonyl, oxygen and/or nitrogen in the chain); an alkenyl of 2 to 24 carbon atoms (which may optionally be substituted by hydroxyl, carboxyl and/or amino group(s) and/or contain carbonyl, oxygen and/or nitrogen in the chain); a cycloalkyl of 5 to 12 carbon atoms (which may optionally be substituted by hydroxyl, carboxyl and/or amino group(s) and/or contain carbonyl, oxygen and/or nitrogen in the ring); and —OR. Still more preferably, each $R^3$ is independently selected from hydrogen, an alkyl of 1 to 24 carbon atoms optionally containing an oxygen atom in the chain, a hydroxyalkyl of 1 to 24 carbon atoms optionally containing an oxygen atom in the chain and —OR. Especially preferred is when each $R^3$ is independently selected from hydrogen, an alkyl of 1 to 4 carbon atoms and —OR; particularly hydrogen, methyl and —OR; and most particularly hydrogen and methyl.

In preferred embodiments, each $R^4$, $R^{4'}$ and $R^{4''}$ is independently selected from hydrogen, a hydrocarbyl group of 1 to 24 carbon atoms, a hydrocarbyloxy group of 1 to 24 carbon atoms, an acyl group of 2 to 24 carbon atoms and an acyloxy group of 2 to 24 carbon atoms. More preferably, each $R^4$, $R^{4'}$ and $R^{4''}$ is independently selected from hydrogen; an alkyl of 1 to 24 carbon atoms optionally containing an oxygen atom in the chain; an alkyloxy of 1 to 24 carbon atoms optionally containing an oxygen atom in the chain; an alkenyl of 2 to 24 carbon atoms optionally containing an oxygen atom in the chain; an alkenyloxy of 2 to 24 carbon atoms optionally containing an oxygen atom in the chain; an acyl group of 2 to 12 carbon atoms; and an acyloxy group of 2 to 12 carbon atoms. Still more preferably, each $R^4$, $R^{4'}$ and $R^{4''}$ is independently selected from hydrogen, an alkyl of 1 to 8 carbon atoms, an alkyloxy of 1 to 8 carbon atoms optionally containing an oxygen atom in the chain, a hydroxyalkyl of 1 to 8 carbon atoms optionally containing an oxygen atom in the chain, a hydroxyalkyloxy of 1 to 8 carbon atoms optionally containing an oxygen atom in the chain, an acyl group of 2 to 12 carbon atoms and an acyloxy of 2 to 12 carbon atoms. Especially preferred is when each $R^4$, $R^{4'}$ and $R^{4''}$ is independently selected from hydrogen and an alkyl of 1 to 4 carbon atoms, and particularly hydrogen and methyl.

In preferred embodiments, each of $R^5$ and $R^9$ is independently a hydrocarbylene group of 1 to 50 carbon atoms, and particularly 1 to 24 carbon atoms. More preferably, each of $R^5$ and $R^9$ is independently selected from an alkylene having a total of 1 to 24 carbon atoms (which may optionally contain carbonyl and/or oxygen in the chain, and/or possess a functional group); an alkenylene having a total of 2 to 24 carbon atoms (which may optionally contain carbonyl and/or oxygen in the chain, and/or possess a functional group) and a cycloalkylene having a total 5 to 24 carbon atoms (which may optionally contain carbonyl and/or oxygen in the ring, and/or possess a functional group). Still more preferably, each of $R^5$ and $R^9$ is independently an alkylene having a total of 1 to 24 carbon atoms (optionally containing an oxygen atom in the chain and/or possessing a functional group) and especially an alkylene of 2 to 18 carbon atoms (optionally containing an oxygen in the chain and/or possessing a functional group). For clarification, the total of carbon atoms mentioned above includes the carbon atoms present in a functional group.

In preferred embodiments, $R^6$ is H.

In preferred embodiments, each of $R^7$, $R^8$ and $R^{10}$ is independently selected from hydrogen, a hydrocarbyl group of 1 to 50 carbon atoms and a functional hydrocarbyl group of 1 to 50 carbon atoms. More preferably, each of $R^7$, $R^8$ and $R^{10}$ is independently selected from hydrogen, an alkyl having a total of 1 to 24 carbon atoms (which may optionally be substituted by a hydroxyl, and/or contain carbonyl, oxygen and/or nitrogen in the chain); an alkenyl having a total of 2 to 24 carbon atoms (which may optionally be substituted by hydroxyl and/or contain carbonyl, oxygen and/or nitrogen in the chain); a cycloalkyl having a total 5 to 12 carbon atoms (which may optionally be substituted by a hydroxyl and/or contain carbonyl, oxygen and/or nitrogen in the ring); and an aralkyl having a total of 7 to 24 carbon atoms (which may optionally be substituted with a hydroxyl). Still more preferably, each of $R^7$, $R^8$ and $R^{10}$ is independently selected from hydrogen and an alkyl of 1 to 24 carbon atoms optionally containing an oxygen atom in the chain. Especially preferred is when each of $R^7$, $R^8$ and $R^{10}$ is independently selected from hydrogen and an alkyl of 1 to 12 carbon atoms.

In preferred embodiments, A is selected from —O(O)O— and —C(O)—; each of $A^1$ and $A^3$ is independently selected from —COOR$^7$, —COO$^-$M$^+$, —C(O)R$^7$, —C(O)NR$^7$R$^8$ and —CN; and $A^2$ is selected from —C(O)—; —R$^9$C(O)— and —R$^9$OC(O)—.

In preferred embodiments, M$^+$ is a cationic group preferably derived from a compound selected from a tertiary amine, ammonia, an alkali metal and an alkaline earth metal.

Finally, further preferred embodiments may include any combination of the parameters mentioned above.

Particularly preferred embodiments of the trisaryl-1,3,5-triazines of the general formula (I) are exemplified by the following structures (VII), (IX) and (X):

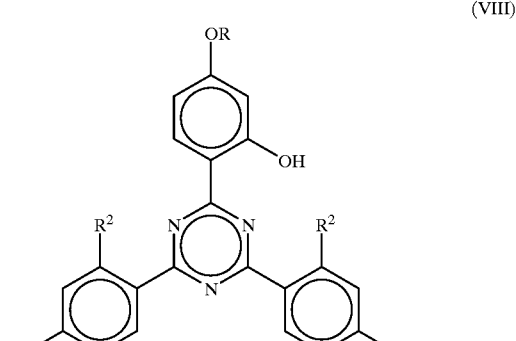

(VIII)

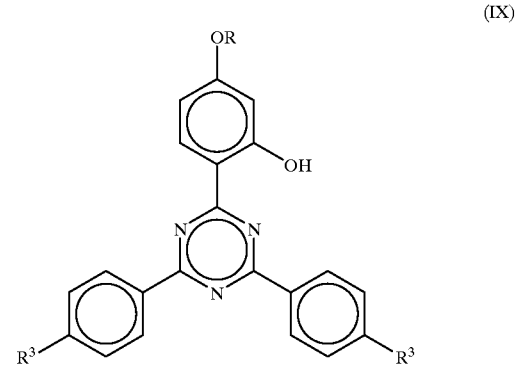

(IX)

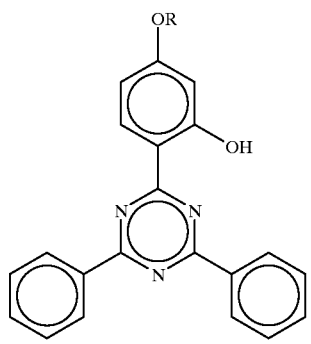
(X)

Particularly preferred embodiments of the trisaryl-1,3,5-triazines of the general formula (II) are exemplified by the following structures (XI), (XII) and (XIII):

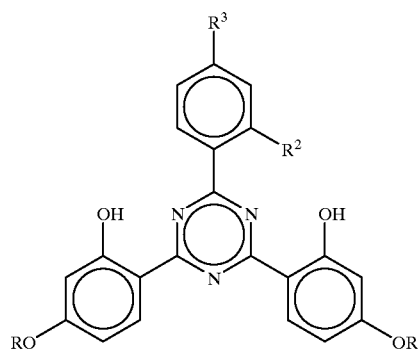
(XI)

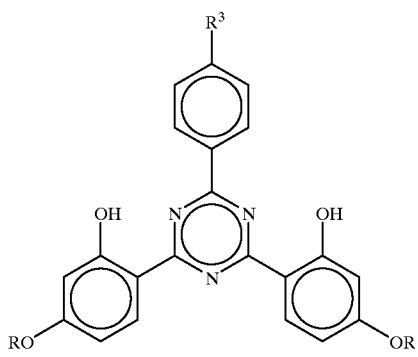
(XII)

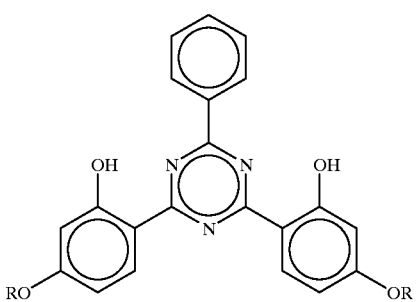
(XIII)

Particularly preferred embodiments of the trisaryl-1,3,5-triazines of the general formula (III) are exemplified by the following structure (XIV):

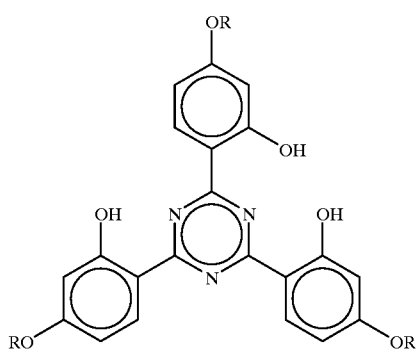
(XIV)

Particularly preferred embodiments of groups of the general formula (V) include the following:

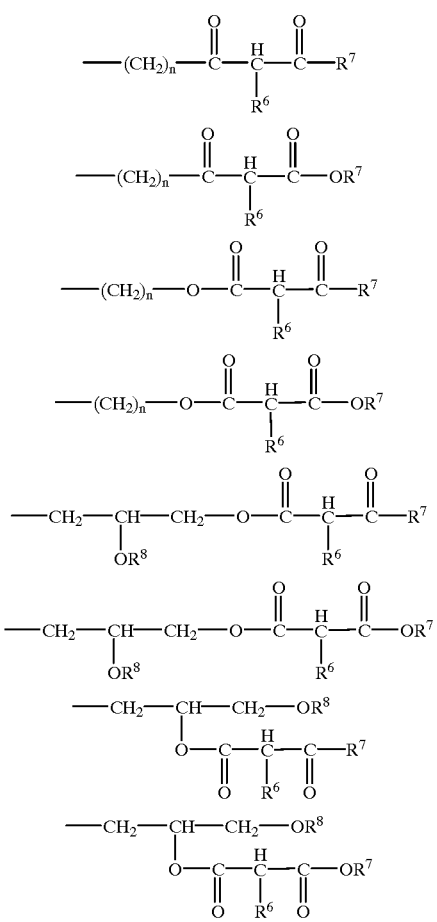

wherein each of $R^6$, $R^7$ and $R^8$ are individually as defined above (both broadly and preferably), and n is 1–24, preferably 1–18 and especially 1–8.

Particularly preferred embodiments of groups of the general formula (VI) include the following:

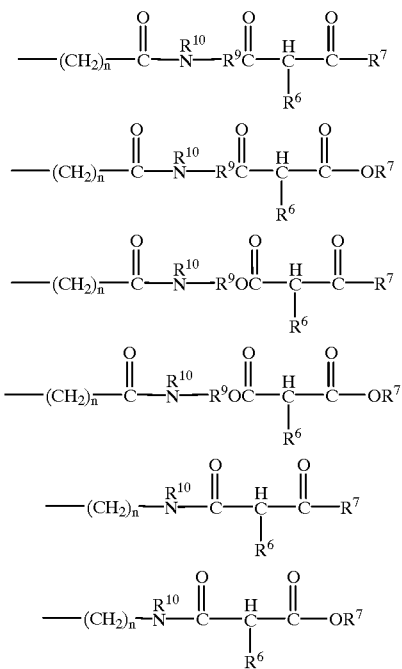

wherein each of $R^6$, $R^7$, $R^9$ and $R^{10}$ are individually as defined above (both broadly and preferably, and n is 1–24, preferably 1–18 and especially 1–8.

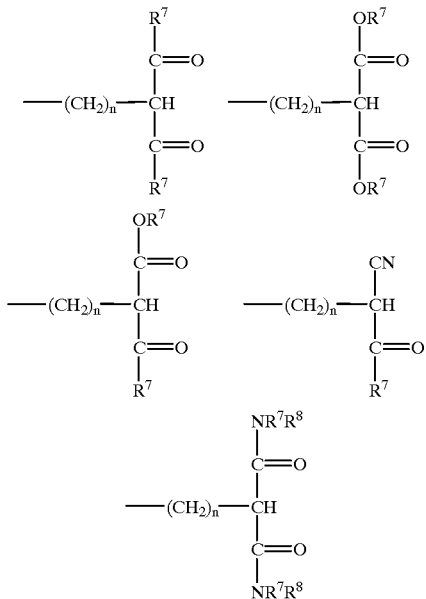

wherein
$R^7$ and $R^8$ are independently as defined above (both broadly and preferably), and
n is 1–24, preferably 1–18 and especially 1–8.

Methods of Preparation

The trisaryl-1,3,5-triazines of the present invention can be prepared by a multistep process in which a precursor compound, having at least one aryl ring with an amino, amido and/or hydroxyl group containing —OR moiety para to the point of attachment of the aryl ring to the triazine ring, is appropriately functionalized, by analogy to the procedures described in a number of the previously incorporated references such as U.S. Pat. No. 3,244,708 and EP-A-0434608.

In a preferred method for preparing a compound containing a group of the formula (V) and/or (VI), a precursor compound corresponding to the formulas (I), (II) or (III), except where at least one (and preferably all) R groups are hydroxyalkyl, aminoalkyl, glycidyl and/or N-hydroxyalkylamido, is reacted with an active methylene and/or active methine group containing compound to prepare the desired product.

In another preferred method for preparing a compound containing a group of the formula (V) and/or (VI), a precursor compound corresponding to the formulas (I), (II) or (III), except where at least one (and preferably all) R groups are hydrogen, is reacted with an active methylene containing precursor derived by reacting an active methylene group containing compound (such as, for example, an alkylacetoacetate, haloacetoacetate or dialkyl malonate) with, for example, a dihaloalkyl compound or haloalcohol.

In a preferred method for preparing a compound containing a group of the formula (VII), a precursor compound corresponding to the formulas (I), (II) or (III), except where at least one (and preferably all) R groups are hydrogen, is reacted with a monohalo, active methine containing precursor derived by reaction an active methylene group containing compound with, for example, a dihaloalkyl compound.

As suitable examples of active methylene and/or active methine group-containing compounds may be mentioned alkyl and halo acetoacetates such as methyl, ethyl, propyl, isopropyl, butyl, isobutyl and chloro acetoacetate; malonic acid, malonic anhydride, and the mono- and di-esters, halo and/or amides thereof, such as dimethyl malonate, diethyl malonate, dimethyl methoxymalonate, dimethyl methylmalonate, diethyl methylmalonate, malonoyl dichloride and malonamide.

The reaction of the precursor compound with the active methylene and/or active methine containing compound, as well as the preparation of the active methylene and/or active methine containing precursors, may be conducted under appropriate esterification, transesterification and/or acylating conditions known to those of ordinary skill in the art. Preferably, the reaction is carried out in the presence of an inert solvent, such as acetonitrile, acetone, methyl ethyl ketone, methyl isobutyl ketone, dimethylformamide, dioxane, tetrahydrofuran, and aromatic hydrocarbons such as toluene and xylene. The reaction is also preferably carried out in the presence of (trans)esterification/acylation catalysts including the titanates such as tetra-i-propyltitanate (TYZOR® TPT) (titanium (IV) isoproxide) tetrabutyltitanate (TYZOR® TBT) (titanium (IV) butoxide), alkali and alkaline earth salts of β-ketoesters and β-diketones such as calcium and magnesium salts of acetoacetic acid, alkoxides and oxides of alkali and alkaline earth metals such as sodium, potassium, calcium and magnesium, tertiary amines such as 4-dimethylaminopyridine), and strong protonic acids such as $H_2SO_4$, HCl and p-toluenesulfonic acid, which may optionally be supported on inert supports, and transition metal salts such as zinc, nickel, copper or cobalt acetate. The reaction is preferably carried out under reflux conditions, with the removal of volatile alcohol and other by-products.

Specific preferred preparative procedures are detailed in the examples annexed hereto.

Uses of the Trisaryl-1,3,5-Triazines

As indicated earlier, the novel trisaryl-1,3,5-triazines of the present invention are particularly useful as ultraviolet light absorber agents for stabilizing a wide variety of materials including, for example, various polymers (both crosslinked and thermoplastic), photographic materials and dye solutions for textile materials, as well as in ultraviolet light screening agents (such as sunscreens). The trisaryl-1,3,5-triazines of the present invention can be incorporated into such material in any one of a variety of conventional manners, including for example, physical mixing or blending, optionally, with chemical bonding to the material (typically to a polymer), as a component in a light stabilizing composition such as a coating or solution, or as a component in a UV screening composition such as a sunscreen composition.

In one embodiment of the present invention, the trisaryl-1,3,5-triazines of the present invention can be employed to stabilize materials which are subject to degradation by ultraviolet radiation by incorporating the presently claimed compounds into such materials, especially organic polymers, either chemically or physically. Examples of polymers which can be stabilized include, but are not limited to:

1. Homo- and copolymers of monoolefins and diolefins including but not limited to ethylene, propylene, isobutylene, butene, methylpentene, hexene, heptene, octene, isoprene, butadiene, hexadiene, dicyclopentadiene, ethylidene and cycloolefins such as cyclopentene and norbornene; for example, polyethylenes (which optionally can be crosslinked) such as high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE) and branched low density polyethylene (BLDPE).
2. Copolymers of one or more monoolefins and/or diolefins with carbon monoxide and/or with other vinyl monomers, including but not limited to acrylic and methacrylic acid, acrylates and methacrylates, acrylamides, acrylonitriles, styrenes, vinyl acetate (such as ethylene/vinyl acetate copolymers), vinyl halides, vinylidene halides, maleic anhydride and allyl monomers such as allyl alcohol, allyl amine, allyl glycidyl ether and derivatives thereof.
3. Hydrocarbon resins (such as $C_5$–$C_9$) including hydrogenated modifications thereof and mixtures of polyalkylenes and starch.
4. Homo- and copolymers of styrenes such as styrene, p-methylstyrene and αmethylstyrene.
5. Copolymers of one or more styrenes with other vinyl monomers such as olefins and diolefins (e.g., ethylene, isoprene and/or butadiene), acrylic and methacrylic acid, acrylates and methacrylates, acrylamides, acrylonitriles, vinyl acetate (such as ethylene/vinyl acetate copolymers), vinyl halides, vinylidene halides, maleic anhydride and allyl compounds such as allyl alcohol, allyl amine, allyl glycidyl ether and derivatives thereof.
6. Graft copolymers of styrenes on polybutadienes, polybutadiene/styrene copolymers and polybutadiene/acrylonitrile copolymers; styrene (or α-methylstyrene) and acrylonitrile (or methacrylonitrile) on polybutadiene; styrene and maleic anhydride on polybutadiene; styrene, acrylonitrile and maleic anhydride or maleimide on polybutadiene; styrene and acrylonitrile on ethylene/propylene/diene copolymers; styrene and acrylonitrile on polyalkyl acrylates or methacrylates; and styrene and acrylonitrile on acrylatelbutadiene copolymers.
7. Halogen-containing polymers such as polychloroprene; chlorinated rubbers; chlorinated and brominated isobutylene/isoprene copolymers; chlorinated or sulfochlorinated polyethylene; copolymers of ethylene and chlorinated ethylene; epichlorohydrin polymers and copolymers; and polymers and copolymers of halogen-containing vinyl compounds such as vinyl chloride, vinylidene chloride, vinyl fluoride and/or vinylidene fluoride and other vinyl monomers.
8. Homo- and copolymers derived from α,β-unsaturated acids and derivatives thereof such as acrylic acid, methacrylic acid, acrylates, methacrylates, acrylamides and acrylonitriles.
9. Copolymers of the monomers mentioned in (8) with other unsaturated monomers such as olefins and diolefins (e.g., butadiene), styrenes, vinyl halides, maleic anhydride and allyl monomers such as allyl alcohol, allyl amine, allyl glycidyl ether and derivatives thereof.
10. Homo- and copolymers derived from unsaturated alcohols and amines or the acyl derivatives or acetals thereof, such as vinyl alcohol, vinyl acetate, vinyl stearate, vinyl benzoate, vinyl maleate, vinyl butyral, allyl alcohol, allyl amine, allyl glycidyl ether, allyl phthalate and allyl melamine; as well as copolymers of such monomers with other ethylenically unsaturated monomers mentioned above.
11. Homo- and copolymers of cyclic ethers such as alkylene glycols and alkylene oxides, as well as copolymers with bisglycidyl ethers.
12. Polyacetals such as polyoxymethylene and those polyoxymethylenes which contain ethylene oxide as a comonomer; and polyoxymethylenes modified with thermoplastic polyurethanes, acrylates and/or MBS.
13. Polyphenylene oxides and sulfides.
14. Polyurethanes derived from hydroxy-functional components such as polyhydric alcohols, polyethers, polyesters, polyacrylics and/or polybutadienes on the one hand, and aliphatic and/or aromatic isocyanates on the other, as well as precursors thereof.
15. Polyamides and copolyamides derived from diamines, dicarboxylic acids and/or aminocarboxylic acids or the corresponding lactams, such as polyamide 4, polyamide 6, polyamide 6/6, polyamide 6/10, polyamide 6/9, polyamide 6/12, polyamide 4/6, polyamide 12/12, polyamide 11 and polyamide 12; aromatic polyamides starting from m-xylene diamine and adipic acid; polyamides prepared from hexamethylene diamine and isophthalic and/or terephthalic acid and with or without an elastomer as a modifier, for example, poly-2,4,4-trimethylhexamethylene terephthalamide or poly-m-phenylene isophthalamide; block copolymers of the aforementioned polyamides with polyolefins, olefin copolymers, ionomers, chemically bonded or grafted elastomers, or polyethers such as polyethylene glycol, polypropylene glycol or polytetramethylene glycol; and polyamides condensed during processing (RIM polyamide systems).
16. Polyureas, polyimides, polyamide-imides, polyetherimides, polyesterimides, polyhydantoins and polybenzimidazoles.
17. Polyesters derived from dicarboxylic acids, diols and/or hydroxycarboxylic acids or the corresponding lactones, such as polyethylene terephthalate, polybutylene terephthalate, poly-1,4-dimethylcyclohexane terephthalate and polyhydroxybenzoates, as well as block copolyether esters derived from hydroxyl-terminated ethers; and also polyesters modified with polycarbonate or MBS.
18. Polycarbonates and polyester carbonates.
19. Polysulfones, polyether sulfones and polyether ketones.
20. Crosslinked polymers derived from aldehydes condensation resins such as phenol/formaldehyde resins, urea/formaldehyde resins and melamine/formaldehyde resins.

21. Drying and non-drying alkyd resins.
22. Unsaturated polyester resins derived from copolyesters of saturated and unsaturated dicarboxylic acids with polyhydric alcohols and vinyl compounds as crosslinking agents and also halogen-containing modifications thereof.
23. Crosslinkable acrylic resins derived from substituted acrylates such as epoxy acrylates, hydroxy acrylates, isocyanato acrylates, urethane acrylates or polyester acrylates.
24. Alkyd resins, polyester resins and acrylate resins crosslinked with melamine resins, urea resins, isocyanates, isocyanurates, carbamates or epoxy resins.
25. Crosslinked epoxy resins derived from aliphatic, cycloaliphatic, heterocyclic and/or aromatic glycidyl compounds such as bisphenol A and bisphenol F, which are crosslinked with customary hardeners such as anhydrides or amines.
26. Natural polymers such as cellulose, rubber, gelatin and chemically modified homologous derivatives thereof, including cellulose acetates, cellulose propionates and cellulose butyrates, or the cellulose ethers such as methyl cellulose, as well as rosins and their derivatives.
27. Polysiloxanes.
28. Michael addition polymers of amines or blocked amines (e.g., ketimines) with activated unsaturated and/or methylene compounds such as acrylates and methacrylates, maleates and acetoacetates.
29. Mixtures or blends of any of the above, such as PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylate, POM/thermoplastic PUR, PC/thermoplastic polyurethane, POM/acrylate, POM/MBS, PPO/HIPS, PPO/PA6.6 and copolymers, PA/HDPE, PP/HDPE, PP/LDPE, LDPE/HDPE, LDPE/EVA, LDPE/EAA, PA/PP, PA/PPO, PBT/PC/ABS, PBT/PET/PC and the like.
30. Polyketimines in combination with unsaturated acrylic polyacetoacetate resins or with unsaturated acrylic resins including urethane acrylates, polyether acrylates, vinyl or acryl copolymers with pendant unsaturated groups and acrylated melamines.
31. Radiation curable compositions containing ethylenically unsaturated monomers or oligomers and a polyunsaturated aliphatic oligomer.
32. Epoxymelamine resins such as light-stable epoxy resins cross-linked by an epoxy functional coetherified high solids melamine resin.

Other materials which can be stabilized include, for example:

33. Naturally occurring and synthetic organic materials which may be mixtures of compounds, including mineral oils, animal and vegetable fats, oils and waxes, or oils, fats or waxes based on synthetic esters (e.g., phthalates, adipates, phosphates or trimellitates) and also mixtures of synthetic esters with mineral oils in any ratio.
34. Aqueous emulsions of natural or synthetic rubber such as natural latex or lattices of carboxylated styrene/butadiene copolymers.
35. Organic dyes such as azo dyes (diazo, triazo and polyazo), anthraquinones, benzodifuranones, polycyclic aromatic carbonyl dyes, indigoid dyes, polymethines, styryl dyes, di- and triaryl carbonium dyes, phthalocyanines, quinophthalones, sulfur dyes, nitro and nitroso dyes, stilbene dyes, formazan dyes, quinacridones, carbazoles and perylene tetracarboxylic diimides.
36. Cosmetic products, such as skin lotions, collagen creams, sunscreen, facial make-up, etc., comprising synthetic materials such as antioxidants, preservatives, lipids, solvents, surfactants, colorants, antiperspirants, skin conditioners, moisturizers etc.; as well as natural products such as collagen, proteins, mink oil, olive oil, coconut oil, carnauba wax, beeswax, lanolin, cocoa butter, xanthan gum, aloe, etc.
37. Cellulose-based paper formulations for use, e.g., in newsprint, cardboard, posters, packaging, labels, stationery, book and magazine paper, bond typing paper, multi-purpose and office paper, computer paper, xerographic paper, laser and ink-jet printer paper, offset paper, currency paper, etc.
38. Photographic film paper.
39. Ink.

As mentioned above, one particular advantage of the trisaryl-1,3,5-triazines of the present invention is that they can be chemically bound to substrates, such as polymers, thereby greatly reducing the migration of such UV absorbers, e.g., out of the substrate or away from the substrate surface. The bonding mechanism of the triazines of the present invention involves the formation of a bond (chemical and/or co-valent) between the active methylene and/or methine group and the "host" substrate, such as a polymer.

Incorporation of the trisaryl-1,3,5-triazines of the invention can be brought about by copolymerization, copolyaddition, copolycondensation, by reaction with a polymer which carries suitable functional groups, or by grafting, in a manner as disclosed in previously incorporated U.S. Pat. No. 3,423,360 and U.S. Pat. No. 5,189,084.

Bonding of the trisaryl-1,3,5-triazines of the invention can occur by polymerization or copolymerization. Polymerization or copolymerization can be carried out in solution, in an emulsion, in a dispersion, in the melt, or in the solid state as is well known to those in the polymerization art.

In addition, bonding of the present trisaryl-1,3,5-triazine compounds of the present invention of the formulas (I), (II), or (III) can be brought about by copolyaddition or copolycondensation. Such incorporation can be made by addition during the synthesis of an addition polymer or copolymer or by condensation during the synthesis of a condensation polymer or copolymer by methods known to those skilled in the art. For example, compounds of the formulas (I), (II), or (III) containing the appropriate functional groups can be incorporated into polyesters, polyamides, polyurethanes, epoxy resins, melamine resins, alkyd resins, phenolic resins, polyurethanes, polycarbonates, polysiloxanes, polyacetals and polyanhydrides, to name but a few.

In addition, compounds of the formulas (I), (II), or (III) can be bonded to a monomeric component which is then incorporated into a polymer or copolymer, e.g., by the free radical initiated addition or copolycondensation methods described above. Analagous methods are disclosed in, for example, U.S. Pat. No. 5,459,222 (incorporated by reference herein for all purposes as if fully set forth) for the bonding of benzotriazole and benzophenone stabilizers to diol precursors which are then incorporated by condensation polymerization into polyurethanes and polyesters to impart UV stabilizing properties to said polymers.

Alternately, the trisaryl-1,3,5-triazines of the invention may also be bonded to polymers by reaction with an oligomer and/or polymer which carries suitable functional groups. For example, the present triazine compounds may be reacted by Michael addition to compounds or polymers containing pendant activated unsaturated groups. The present triazine compounds may also be reacted with a polymer and/or oligomer such as polyesters, polyurethanes and polydiols with other appropriate reactive end-groups, partially hydrolyzed polyvinylacetate, epoxy resins, polysiloxanes and polymers comprising maleic anhydride, either in the main chain or as a side-chain, by methods analagous to those well known to those of ordinary skill in the art.

Grafting is yet another way of bonding of the present trisaryl-1,3,5-triazine compounds of the formulas (I), (II), or (III) to polymers and/or oligomers. Grafting may be carried out in solution, in the melt, or in the solid state to saturated polymers, e.g., polyolefins and their copolymers such as polyethylene, polypropylene and poly(ethylene-vinyl acetate), or to polymers comprising unsaturated moieties, e.g., polybutadiene, polyisoprene, ethylene-propylene-(diene monomer) terpolymers and polystyrene and its copolymers.

The trisaryl-1,3,5-triazines of the present invention may be used in widely varying amounts in such applications depending upon such things as the material to be stabilized and the particular application. However, when employed as a stabilizing additive for materials such as organic polymers, the trisaryl-1,3,5-triazines of the present invention are typically employed in amounts from about 0.01 to about 20% by weight, preferably from about 0.1 to about 10% by weight, and most preferably from about 0.1 to about 5% by weight, based on the weight of the material to be stabilized. In screening applications such as sunscreening compositions, the triazines are utilized in the same relative amounts but based on the total weight of the screening agent.

The novel stabilizers of the present invention may also be employed in a nonbondable capacity, for example, in the stabilization of thermoplastic polymers as set forth in the many of the previously incorporated references. Examples of preferred thermoplastic polymers are polyolefins and polymers comprising heteroatoms in the main chain. Preferred polymers are also thermoplastic polymers comprising nitrogen, oxygen and/or sulphur, especially nitrogen or oxygen, in the main chain. Also of interest are compositions in which the polymer is a polyolefin, for example polyethylene or polypropylene.

Incorporation into the thermoplastic polymers can be carried out by addition of the triazine compounds and any further additives by the methods conventional in the art. The incorporation can expediently be made before or during shaping, for example by mixing the pulverulent components or by adding the stabilizer to the melt or solution of the polymer, or by applying the dissolved or dispersed compounds to the polymer, with or without subsequent evaporation of the solvent. Elastomers can also be stabilized as lattices.

The novel mixtures can also be added to the polymers to be stabilized in the form of a masterbatch which comprises these compounds, for example, in a concentration of from about 2.5 to about 25%, preferably from about 5 to about 20% by weight of the polymer.

The novel mixtures can expediently be incorporated into the polymeric material by any number of methods, including those conventionally employed in the art, including, for example: (a) as an emulsion or dispersion (for example to lattices or emulsion polymers); (b) as a dry mix during mixing of additional components or polymer mixtures; (c) by direct addition to the processing equipment (for example extruders, internal mixers, etc.); or (d) as a solution or melt.

The stabilized polymer compositions obtained in this way can be converted into shaped articles, for example fibers, films, tapes, sheets, sandwich boards, containers, pipes and other profiles, by any number of conventional methods, for example hot pressing, spinning, extrusion, roto-molding or injection molding. Therefore, the present invention additionally relates to the use of the polymer composition according to the invention for the production of a shaped article.

Depending upon their ultimate end use, the trisaryl-1,3,5-triazines of the present invention may be combined with a variety of additives conventionally employed in the UV stabilizing art. Examples of such additives include but are not limited to:

(a.) Antioxidants (i) Alkylated monophenols such as 2,6-di-tert-butyl-4-methylphenol; 2-tert-butyl-4,6-dimethylphenol; 2,6-di-tert-butyl-4-ethylphenol; 2,6-di-tert-butyl-4-n-butylphenol; 2,6-di-tert-butyl-4-isobutylphenol; 2,6-dicyclopentyl-4-methylphenol; 2-(α-methylcyclohexyl)-4,6-dimethylphenol; 2,6-dioctadecyl-4-methylphenol; 2,4,6-tricyclohexylphenol; 2,6-di-tert-butyl-4-methoxymethylphenol; nonylphenols which are liner or branched in the side chains such as 2,6-di-nonyl-4-methylphenol; 2,4-dimethyl-6-(1-methylheptadec-1-yl)phenol; 2,4-dimethyl-6-(1-methylheptadec-1-yl)phenol; 2,4-dimethyl-6-(1-methyltridec-1-yl)phenol; and mixtures thereof.

(ii) Alkylthiomethylphenols such as 2,4-dioctylthiomethyl-6-tert-butylphenol; 2,4-dioctylthiomethyl-6-methylphenol; 2,4-dioctylthiomethyl-6-ethylphenol; and 2,6-di-dodecylthiomethyl-4-nonylphenol.

(iii) Hydroquinones and alkylated hydroquinones such as 2,6-di-tert-butyl-4-methoxyphenol; 2,5-di-tert-butylhydroquinone; 2,5-di-tert-amylhydroquinone; 2,6-diphenyl-4-octadecyloxyphenol; 2,6-di-tert-butylhydroquinone; 2,5-di-tert-butyl-4-hydroxyanisole; 3,5-di-tert-butyl-4-hydroxyanisole; 3,5-di-tert-butyl-4-hydroxyphenylstearate; and bis(3,5-di-tert-butyl-4-hydroxyphenyl)adipate.

(iv) Tocopherols such as α-tocopherol, βtocopherol, γ-tocopherol, δ-tocopherol and mixtures thereof (vitamin E).

(v) Hydroxylated thiodiphenyl ethers such as 2,2'-thiobis(6-tert-butyl-4-methylphenol); 2,2'-thiobis(4-octylphenol); 4,4'-thiobis(6-tert-butyl-3-methylphenol); 4,4'-thiobis(6-tert-butyl-2-methylphenol); 4,4'-thiobis(3,6-di-sec-amylphenol); and 4,4'-bis(2,6-dimethyl-4-hydroxyphenyl)disulfide.

(vi) Alkylidenebisphenols such as 2,2'-methylenebis(6-tert-butyl-4-methylphenol); 2,2'-methylenebis(6-tert-butyl-4-ethylphenol); 2,2'-methylenebis[4-methyl-6-(α-methylcyclohexyl)phenol]; 2,2'-methylenebis(4-methyl-6-cyclohexylphenol); 2,2'-methylenebis(6-nonyl-4-methylphenol); 2,2'-methylenebis(4,6-di-tert-butylphenol); 2,2'-ethylidenebis(4,6-di-tert-butylphenol); 2,2'-ethylidenebis(6-tert-butyl-4-isobutylphenol); 2,2'-methylenebis[6-(α-methylbenzyl)-4-nonylphenol]; 2,2'-methylenebis[6-(α,α-dimethylbenzyl)-4-nonylphenol]; 4,4'-methylenebis(2,6-di-tert-butylphenol); 4,4'-methylenebis(6-tert-butyl-2-methylphenol); 1,1-bis(5-tert-butyl-4-hydroxy-2-methylphenyl)butane; 2,6-bis(3-tert-butyl-5-methyl-2-hydroxybenzyl)-4-methylphenol; 1,1,3-tris(5-tert-butyl-4-hydroxy-2-methylphenyl)butane; 1,1-bis(5-tert-butyl-4-hydroxy-2-methylphenyl)-3-n-dodecylmercaptobutane; ethylene glycol bis[3,3-bis(3'-tert-butyl-4'-hydroxyphenyl)butyrate], bis(3-tert-butyl-4-hydroxy-5-methylphenyl)dicyclopentadiene; bis[2-(3'-tert-butyl-2'-hydroxy-5'-methylbenzyl)-6-tert-butyl-4-methylphenyl]terephthalate; 1,1-bis(3,5-dimethyl-2-hydroxyphenyl)butane; 2,2-bis(3,5-di-tert-butyl-4-hydroxyphenyl)propane; 2,2-bis(5-tert-butyl-4-hydroxy-2-methylphenyl)-4-n-dodecylmercaptobutane; and 1,1,5,5-tetra(5-tert-butyl-4-hydroxy-2-methylphenyl)pentane.

(vii) O- and S-benzyl compounds such as 3,5,3',5'-tetra-tert-butyl-4,4'-dihydroxydi-benzyl ether; octadecyl-4-hydroxy-3,5-dimethylbenzylmercaptoacetate; tridecyl-4-hydroxy-3,5-di-tert-butylbenzylmercaptoacetate; tris(3,5-di-tert-butyl-4-hydroxybenzyl)amine; bis(4-tert-butyl-3-hydroxy-2,6-dimethylbenzyl)dithioterephthalate; bis(3,5-di-tert-butyl-4-hydroxybenzyl)sulfide; and isooctyl-3,5-di-tert-butyl-4-hydroxybenzylmercaptoacetate.

(viii) Hydroxybenzylate malonates such as dioctadecyl-2,2-bis(3,5-di-tert-butyl-2-hydroxybenzyl)malonate; dioctadecyl-2-(3-tert-butyl-4-hydroxy-5-methylbenzyl)malonate; didodecylmercaptoethyl-2,2-bis(3,5-di-tert-butyl-4-hydroxybenzyl)malonate; and bis[4-(1,1,3,3-tetramethylbutyl)phenyl]-2,2-bis(3,5-di-tert-butyl-4-hydroxybenzyl)malonate.

(ix) Aromatic hydroxybenzyl compounds such as 1,3,5-tris(3,5-di-tert-butyl-4-hydroxybenzyl)-2,4,6-trimethylbenzene; 1,4-bis(3,5-di-tert-butyl-4-hydroxybenzyl)-2,3,5,6-tetramethylbenzene; and 2,4,6-tris(3,5-di-tert-butyl-4-hydroxybenzyl)phenol.

(x) Triazine compounds such as 2,4-bis(octylmercapto-6-(3,5-di-tert-butyl-4-hydroxyanilino)-1,3,5-triazine; 2-octylmercapto-4,6-bis(3,5-di-tert-butyl-4-hydroxyanilino)-1,3,5-triazine; 2-octylmercapto-4,6-bis(3,5-di-tert-butyl-4-hydroxyphenoxy)-1,3,5-triazine; 2,4,6-tris(3,5-di-tert-butyl-4-hydroxyphenoxy)-1,3,5-triazine; 1,3,5-tris(3,5-di-tert-butyl-4-hydroxybenzyl)isocyanurate; 1,3,5-tris(4-tert-butyl-3-hydroxy-2,6-dimethyl benzyl)isocyanurate; 2,4,6-tris(3,5-di-tert-butyl-4-hydroxyphenylethyl)-1,3,5-triazine; 1,3,5-tris(3,5-di-tert-butyl-4-hydroxyphenylpropionyl)-hexahydro-1,3,5-triazine; and 1,3,5-tris(3,5-dicyclohexyl-4-hydroxybenzyl)isocyanurate.

(xi) Benzylphosphonates such as dimethyl-2,5-di-tert-butyl-4-hydroxybenzylphosphonate; diethyl-3,5-di-tert-butyl-4-hydroxybenzylphosphonate; dioctadecyl-3,5-di-tert-butyl-4-hydroxybenzylphosphonate; dioctadecyl-5-tert-butyl-4-hydroxy-3-methylbenzylphosphonate; and the calcium salt of the monoethyl ester of 3,5-di-tert-butyl-4-hydroxybenzylphosphonic acid.

(xii) Acylaminophenols such as 4-hydroxylauranilide; 4-hydroxystearanilide; and octyl N-(3,5-di-tert-butyl-4-hydroxyphenyl)carbamate.

(xiii) Esters of β-(3,5-di-tert-butyl-4-hydroxyphenyl) propionic acid with mono- or polyhydric alcohols such as methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trmethylolpropane and 4-hydroxymethyl-1-phospha-2,6,7-trioxabicyclo[2.2.2]octane.

(xiv) Esters of β-(5-tert-butyl-4-hydroxy-3-methylphenyl) propionic acid with mono- or polyhydric alcohols such as methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane and 4-hydroxymethyl-1-phospha-2,6,7-trioxabicyclo[2.2.2]octane.

(xv) Esters of β-(3,5-dicyclohexyl-4-hydroxyphenyl) propionic acid with mono- or polyhydric alcohols such as methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N, N'-bis(hydroxyethyl)-oxamide, 3-thiaundecanol, 3-thiapentadecanol, trimethylhexanediol, trimethylolpropane and 4-hydroxymethyl-1-phospha-2,6,7-trioxabicyclo[2.2.2]octane.

(xvi) Esters of 3,5-di-tert-butyl-4-hydroxyphenyl acetic acid with mono- or polyhydric alcohols such as methanol, ethanol, octanol, octadecanol, 1,6-hexanediol, 1,9-nonanediol, ethylene glycol, 1,2-propanediol, neopentyl glycol, thiodiethylene glycol, diethylene glycol, triethyleneglycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane and 4-hydroxymethyl-1-phospha-2,6,7-trioxabicyclo[2.2.2]octane.

(xvii) Amides of β-(3,5-di-tert-butyl-4-hydroxyphenyl) propionic acid such as N,N'-bis(3,5-di-tert-butyl-4-hydroxyphenylpropionyl)hexamethylenediamine; N,N'-bis(3,5-di-tert-butyl-4-hydroxyphenylpropionyl) trimethylenediamine; and N,N'-bis(3,5-di-tert-butyl-4-hydroxyphenylpropionyl)hydrazine.

(xviii) Ascorbic acid (Vitamin C).

(xix) Aminic antioxidants such as N,N'-diisopropyl-p-phenylenediamine; N,N'-di-sec-butyl-p-phenylenediamine; N,N'-bis(1,4-dimethylpentyl)-p-phenylenediamine; N,N'-bis(1-ethyl-3-methylpentyl)-p-phenylenediamine; N,N'-bis(1-methylheptyl)-p-phenylenediamine; N,N'-dicyclohexyl-p-phenylenediamine; N,N'-diphenyl-p-phenylenediamine; N,N'-bis(2-naphthyl)-p-phenylenediamine; N-isopropyl-N'-phenyl-p-phenylenediamine; N-(1,3-dimethylbutyl)-N'-phenyl-p-phenylenediamine; N-(1-methylheptyl)-N'-phenyl-p-phenylenediamine; N-cyclohexyl-N'-phenyl-p-phenylenediamine; 4-(p-toluenesulfonamoyl) diphenylamine; N,N'-dimethyl-N,N'-di-sec-butyl-p-phenylenediamine; diphenylamine; N-allyldiphenylamine; 4-isopropoxydiphenylamine; N-phenyl-1-naphthylamine; N-(4-tert-octylphenyl)-1-naphthylamine; N-phenyl-2-naphthylamine; octylated diphenylamine such as p,p'-di-tertoctyidiphenylamine; 4-n-butylaminophenol; 4-butyrylaminophenol; 4-nonanoylaminophenol; 4-dodecanoylaminophenol; 4-octadecanoylaminophenol; bis(4-methoxyphenyl) amine; 2,6-di-tert-butyl-4-dimethylaminomethylphenol; 2,4'-diaminophenylmethane; 4,4'-diaminodiphenylmethane; N,N,N',N'-tetramethyl-4,4'-diaminodiphenylmethane; 1,2-bis[(2-methylphenyl)amino]ethane; 1,2-bis(phenylamino)propane; o-tolyl) biguanide; bis[4-(1',3'-dimethylbutyl)phenyl]amine; tert-octylated N-phenyl-1-naphthylamine; a mixture of mono- and dialkylated tertbutyl/tert-octyldiphenylamines, a mixture of mono- and dialkylated nonyldiphenylamines; a mixture of mono- and dialkylated dodecyidiphenylamines; a mixture of mono- and dialkytated isopropyl/isohexyldiphenylamines, a mixture of mono- and dialkylated tert-butyldiphenylamines; 2,3-dihydro-3,3-dimethyl-4H-1,4-benzothiazine; phenothiazine; a mixture of mono- and dialkylated tert-buty/tert-octyl phenothiazines; a mixture of mono- and dialkylated tert-octylphenothiazines; Nallylphenothiazine; N,N,N',N'-tetraphenyl-1,4-diaminobut-2-ene; N,N-bis(2,2,6,6-tetramethylpiperid-4-yl)hexamethylenediamine; bis(2,2, 6,6-tetramethylpiperid-4-yl)sebacate; 2,2,6,6-tetramethylpiperidin-4-one; and 2,2,6,6-tetramethylpiperidin-4-ol.

(b) UV-absorbers and light stabilizers (i) 2-(2'-Hydroxyphenyl)benzotriazoles such as 2-(2'-hydroxy-5'-methylphenyl)-benzotriazole; 2-(3',5'-di-tert-butyl-2'-hydroxyphenyl)benzotriazole; 2-(5'-tert-butyl-2'-hydroxyphenol)benzotrazole; 2-(2'-hydroxy-5'-(1,1,3,3-tetramethylbutyl)phenyl)benzotriazole; 2-(3',5'-di-tert-butyl-2'-hydroxyphenyl)-5-chlorobenzotriazole; 2-(3'-tert-butyl-2'-hydroxy-5'-methylphenyl)-5-chloro-benzotriazole; 2-(3'-sec-butyl-5'-tert-butyl-2'-hydroxyphenyl)-benzotriazole; 2-(2'-hydroxy-4'-octoxyphenyl)benzotriazole; 2-(3',5'-di-tert-amyl-2'-hydroxphenyl)benzotriazole; 2-(3',5'-bis(α,α-dimethylbenzyl)-2'-hydroxyphenyl)-benzotriazole; a mixture of 2-(3'-tert-butyl-2'-hydroxy-5'-(2-octyloxycarbonylethyl)phenyl)-5-chloro-benzotriazol, 2-(3'-tert-butyl-5'-[2-(2-ethylhexyloxy)-carbonylethyl]-2'-hydroxyphenyl)-5-chloro-benzotrazole, 2-(3'-tert-butyl-2'-hyd roxy-5'-(2-methoxycarbonylethyl)phenyl)-5-chloro-benzotriazol, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole and 2-(3'-tert-butyl-2'-hydroxy-5'-(2-isooctyloxycarbonylethyl)phenylbenzotriazole; 2,2-methylenebis[4-(1,1,3,3-tetramethylbutyl)-6-benzotriazol-2-ylphenol]; the transesterification product of 2-[3'-tert-butyl-5'-(2-methoxycarbonylethyl)-2'-hydroxyphenyl]benzotriazole with polyethylene glycol 300; and [R—CH$_2$CH—COO(CH$_2$)$_3$]$_2$— where R=3'-tert-butyl-4'-hydroxy-5'-2H-benzotriazol-2-ylphenyl.

(ii) 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivative.

(iii) Esters of substituted and unsubstituted benzoic acids such as 4-tert-butyl-phenyl salicylate; phenyl salicylate; octylphenyl salicylate; dibenzoyl resorcinol; bis(4-tert-butylbenzoyl) resorcinol; benzoyl resorcinol; 2,4-di-tert-butylphenyl 3,5-di-tert-butyl-4-hydroxybenzoate; hexadecyl 3,5-di-tert-butyl-4-hydroxybenzoate; octadecyl 3,5-di-tert-butyl-4-hydroxybenzoate; and 2-methyl-4,6-di-tert-butylphenyl 3,5-di-tert-butyl-4-hydroxybenzoate.

(iv) Acrylates such as ethyl α-cyano-β,β-diphenylacrylate; isooctyl α-cyano-β,β-diphenylacrylate; methyl α-carbomethoxycinnamate; methyl α-cyano-β-methyl-p-methoxycinnamate; butyl α-cyano-β-methyl-p-methoxycinnamate; methyl α-carbomethoxy-p-methoxycinnamate; and N-(β-carbomethoxy-β-cyanovinyl)-2-methylindoline.

(v) Nickel compounds such as nickel complexes of 2,2'-thio-bis-[4-(1,1,3,3-tetramethylbutyl)phenol], including the 1:1 or 1:2 complex, with or without additional ligands such as n-butylamine, triethanolamine or N-cyclohexyldiethanolamine; nickel dibutyldithiocarbamate; nickel salts of monoalkyl esters including the methyl or ethyl ester of 4-hydroxy-3,5-di-tert-butylbenzylphosphonic acid; nickel complexes of ketoximes including 2-hydroxy-4-methylphenyl undecyl ketoxime; and nickel complexes of 1-phenyl-4-lauroyl-5-hydroxypyrazole, with or without additional ligands.

(vi) Sterically hindered amines as well as the N derivatives thereof (e.g., N-alkyl, N-hydroxy, N-alkoxy and N-acyl), such as bis(2,2,6,6-tetramethylpiperidin-4-yl) sebacate; bis(2,2,6,6-tetramethylpiperidin-4-yl)succinate; bis(1,2,2,6,6-pentamethylpiperidin-4-yl)sebacate; bis(1-octyloxy-2,2,6,6-tetramethylpiperidin-4-yl)sebacate; bis(1,2,2,6,6-pentamethylpiperidin-4-yl) n-butyl 3,5-di-tert-butyl-4-hydroxybenzylmalonate; the condensate of 1-(2-hydroxyethyl)-2,2,6,6-tetramethyl-4-hydroxypiperidine and succinic acid; the condensate of N,N'-bis(2,2,6,6-tetramethylpiperidin-4-yl)hexamethylenediamine and 4-tert-octylamino-2,6-dichloro-1,3,5-triazine; tris(2,2,6,6-tetramethylpiperidin-4-yl) nitrilotriacetate; tetrakis(2,2,6,6-tetramethylpiperidin-4-yl)-1,2,3,4-butanetetracarboxylate; 1,1'-(1,2-ethanediyl)bis(3,3,5,5-tetramethylpiperazinone); 4-benzoyl-2,2,6,6-tetramethylpiperidine; 4-stearyloxy-2,2,6,6-tetramethylpiperidine; bis(1,2,2,6,6-pentamethylpiperidyl)-2-n-butyl-2-(2-hydroxy-3,5-di-tert-butylbenzyl)malonate; 3-n-octyl-7,7,9,9-tetramethyl-1,3,8-triazaspiro[4.5]decan-2,4-dione; bis(1-octyloxy-2,2,6,6-tetramethylpiperidyl)sebacate; bis(1-octyloxy-2,2,6,6-tetramethylpiperidyl)succinate; the condensate of N,N'-bis(2,2,6,6-tetramethylpiperidin-4-yl)hexamethylenediamine and 4-morpholino-2,6-dichloro-1,3,5-triazine; the condensate of 2-chloro-4,6-bis(4-n-butylamino-2,2,6,6-tetramethylpiperidyl)-1,3,5-triazine and 1,2-bis(3-aminopropylamino)ethane; the condensate of 2-chloro-4,6-bis(4-n-butylamino-1,2,2,6,6-pentamethylpiperidyl)-1,3,5-triazine and 1,2-bis-(3-aminopropylamino)ethane; 8-acetyl-3-dodecyl-7,7,9,9-tetramethyl-1,3,8-triazaspiro[4.5]decane-2,4-dione; 3-dodecyl-1-(2,2,6,6-tetramethylpiperidin-4-yl) pyrrolidin-2,5-dione; 3-dodecyl-1-(1-ethanoyl-2,2,6,6-tetramethylpiperidin-4-yl)pyrrolidin-2,5-dione; 3-dodecyl-1-(1,2,2,6,6-pentamethylpiperidin-4-yl) pyrrolidine-2,5-dione; a mixture of 4-hexadecyloxy- and 4-stearyloxy-2,2,6,6-tetramethylpiperidine; the condensate of N,N'-bis(2,2,6,6-tetramethylpiperidin-4-yl) hexamethylenediamine and 4-cyclohexylamino-2,6-dichloro-1,3,5-triazine; the condensate of 1,2-bis(3-aminopropylamino)ethane, 2,4,6-trichloro-1,3,5-triazine and 4-butylamino-2,2,6,6-tetramethylpiperidine (CAS Reg. No. [136504-96-6]); 2-undecyl-7,7,9,9-tetramethyl-1-oxa-3,8-diaza-4-oxospiro[4.5]decane; oxo-piperanzinyl-triazines or so-called PIP-T HALS, e.g., GOODRITE® 3034, 3150 and 3159 and similar materials disclosed in U.S. Pat. No. 5,071,981; photobondable HALS such as SANDUVOR® PR-31 and PR-32 (Clariant Corp.) and similar materials disclosed in GB-A-2269819; and the reaction product of 7,7,9,9-tetramethyl-2-cycloundecyl-1-oxa-3,8-diaza-4-oxospiro[4.5]decane and epichlorohydrin. See also generally U.S. Pat. No. 4,619,956, U.S. Pat. No. 5,106,891, GB-A-2269819, EP-A-0309400, EP-A-0309401, EP-A-0309402 and EP-A-0434608, which (to the extent not already done so) are incorporated herein by reference as if fully set forth.

(vii) Oxamides such as 4,4'-dioctyloxyoxanilide; 2,2'-diethoxyoxanilide; 2,2'-dioctyloxy-5,5'-di-tert-butoxanilide; 2,2'-didodecyloxy-5,5'-di-tert-butyloxanilide; 2-ethoxy-2'-ethyloxanilide; N,N'-bis(3-dimethylaminopropyl)oxamide; 2-ethoxy-5-tert-butyl-2'-ethyloxanilide and its mixture with 2-ethoxy-2'-ethyl-5,4'-di-tert-butoxanilide; and mixtures of o- and p-methoxy disubstituted oxanilides and mixtures of o- and pethoxy disubstituted oxanilides.

(viii) 2-(2-Hydroxyphenyl)-1,3,5-triazines disclosed in the previously incorporated references, such as 2,4,6-tris(2-hydroxy-4-octyloxyphenyl)-1,3,5-triazine; 2-(2-hydroxy- 4-n-octyloxyphenyl)-4,6-bis(2,4-dimethylphenyl)-1,3,5-triazine; 2-(2-hydroxy-4-(mixed iso-octyloxyphenyl)-4,6-bis(2,4-dimethylphenyl)-1,3,5-triazine; 2-(2,4-dihydroxyphenyl)-4,6-bis(2,4-dimethylphenyl)-1,3,5-triazine; 2,4-bis(2-hydroxy-4-propyloxyphenyl)-6-(2,4-dimethylphenyl)-1,3,5-triazine; 2-(2-hydroxy-4-octyloxyphenyl)-4,6-bis(4-methylphenyl)-1,3,5-triazine; 2-(2-hydroxy-4-dodecyloxyphenyl)-4,6-bis(2,4-dimethylphenyl)-1,3,5-triazine; 2-(2-hydroxy-4-tridecyloxyphenyl)-4,6-bis(2,4-dimethylphenyl)-1,3,5-triazine; 2-[2-hydroxy-4-(2-hydroxy-3-butyloxypropyloxy)phenyl]-4,6-bis(2,4-dimethylphenyl)-1,3,5-triazine; 2-[2-hydroxy-4-(2-hydroxy-3-octyloxypropyloxy)-phenyl]-4,6-bis(2,4-dimethylphenyl)-1,3,5-trazine; 2-[4-dodecyloxy/tridecyloxy-2-hydroxypropoxy)-2-hydroxyphenyl]-4,6-bis(2,4-dimethylphenyl)-1,3,5-triazine; 2-[2-hydroxy-4-(2-hydroxy-3-dodecyloxypropoxy)phenyl]-4,6-bis(2,4-dimethylphenyl)-1,3,5-triazine; 2-(2-hydroxy-4-hexyloxy)phenyl-4,6-diphenyl-1,3,5-triazine; 2-(2-hydroxy-4-methoxyphenyl)-4,6-diphenyl-1,3,5-triazine; 2,4,6-tris[2-hydroxy-4-(3-butoxy-2-hydroxypropoxy)phenyl-1,3,5-triazine; and 2-(2-hydroxyphenyl)-4-(4-methoxyphenyl)-6-phenyl-1,3,5-triazine.

(c) Metal deactivators such as N,N'-diphenyloxamide; N-salicylal-N'-salicyloyl hydrazine; N,N'-bis(salicyloyl) hydrazine; N,N'-bis(3,5-di-tert-butyl-4-hydroxyphenylpropionyl)hydrazine; 3-salicyloylamino-1,2,4-triazole; bis(benzylidene)oxalyl dihydrazide; oxanilide; isophthaloyl dihydrazide; sebacoyl bisphenylhydrazide; N,N'-diacetyladipoyl dihydrazide; N,N'-bis(salicyloyl) oxalyl dihydrazide; and N,N'-bis(salicyloyl)thiopropionyl dihydrazide.

(d) Phosphites and phosphonites, such as triphenyl phosphite; diphenyl alkyl phosphites; phenyl dialkyl phosphites; tris(nonylphenyl) phosphite; trilauryl phosphite; trioctadecyl phosphite; distearyl pentaerythritol diphosphite; tris(2,4-di-tert-butylphenyl)phosphite; diisodecyl pentaerythritol diphosphite; bis(2,4,-di-tert-butylphenyl)pentaerythritol diphosphite; bis(2,6-di-tert-butyl-4-methylphenyl) pentaerythritol diphosphite; bis(isodecyloxy)pentaerythritol diphosphite; bis(2,4-di-tert-butyl-6-methylphenyl) pentaerythritol diphosphite; bis(2,4,6-tris(tert-butyl)phenyl) pentaerythritol diphosphite; tristearyl sorbitol triphosphite; tetrakis(2,4-di-tert-butylphenyl)-4,4'-biphenylene diphosphonite; 6-isooctyloxy-2,4,8,10-tetra-tert-butyl-12H-dibenzo[d,g]-1,3,2-dioxaphosphocin; 6-fluoro-2,4,8,10-tetra-tert-butyl-12-methyl-dibenzo[d,g]-1,3,2-dioxaphosphocin; bis(2,4-di-tert-butyl-6-methylphenyl) methylphosphite; and bis(2,4-di-tert-butyl-6-methylphenyl) ethylphosphite.

(e) Hydroxylamines such as N,N-dibenzylhydroxylamine; N,N-diethylhydroxylamine; N,N-dioctylhydroxylamine; N,N-dilaurylhydroxylamine; N,N-ditetradecylhydroxylamine; N,N-dihexadecylhydroxylamine; N,N-dioctadecylhydroxylamine; N-hexadecyl-N-otadecylhydroxylamine; N-heptadecyl-N-octadecylhydroxylamine; and N,N-dialkylhydroxylamine derived from hydrogenated tallow fatty amines.

(f) Nitrones such as N-benzyl-alpha-phenyl nitrone; N-ethyl-alpha-methyl nitrone; N-octyl-alpha-heptyl nitrone; N-lauryl-alpha-undecyl nitrone; N-tetradecyl-alpha-tridecyl nitrone; N-hexadecyl-alpha-pentadecyl nitrone; N-octadecyl-alpha-heptadecyl nitrone; N-hexadecyl-alpha-heptadecyl nitrone; N-octadecyl-alpha-pentadecyl nitrone; N-heptadecyl-alpha-heptadecyl nitrone; N-octadecyl-alpha-hexadecyl nitrone; and nitrones derived from N,N-dialkylhydroxylamines prepared from hydrogenated tallow fatty amines.

(g) Thiosynergists such as dilauryl thiodipropionate and distearyl thiodipropionate.

(h) Peroxide scavengers such as esters of β-thiodipropionic acid, for example the lauryl, stearyl, myristyl or tridecyl esters; mercaptobenzimidazole or the zinc salt of 2-mercaptobenzimidazole; zinc dibutyidithiocarbamate; dioctadecyl disulfide; and pentaerythritol tetrakis(β-dodecylmercapto)propionate.

(i) Polyamide stabilizers such as copper salts in combination with iodides and/or phosphorus compounds and salts of divalent manganese.

(j) Basic co-stabilizers such as melamine; polyvinylpyrrolidone; dicyandiamide; triallyl cyanurate; urea derivatives; hydrazine derivatives; amines; polyamides; polyurethanes; alkali metal salts and alkaline earth metal salts of higher fatty acids, for example calcium stearate, zinc stearate, magnesium behenate, magnesium stearate, sodium ricinoleate and potassium palmitate; antimony pyrocatecholate; and tin pyrocatecholate.

(k) Nucleating agents including inorganic substances such as talc and metal oxides (e.g. titanium oxide or magnesium oxide) and phosphates, carbonates and sulfates of, preferably, alkaline earth metals; organic compounds such as mono- or polycarboxylic acids and salts thereof, for example 4-tert-butylbenzoic acid, adipic acid, diphenylacetic acid, sodium succinate and sodium benzoate; and polymeric compounds such as ionic copolymers ("ionomers").

(l) Fillers and reinforcing agents such as calcium carbonate; silicates; glass fibers; asbestos; talc; kaolin; mica; barium sulfate; metal oxides and hydroxides; carbon black; graphite; wood flour and flours or fibers from other natural products; and synthetic fibers.

(m) Other additives such as plasticizers, lubricants, emulsifiers, pigments, rheological additives, catalysts, levelling assistants, optical brighteners, flameproofing agents, antistatic agents and blowing agents.

(n) Benzofuranones and indolinones such as those disclosed in U.S. Pat. No. 4,325,863, U.S. Pat. No. 4,338,244, U.S. Pat. No. 5,175,312, U.S. Pat. No. 5,216,052, U.S. Pat. No. 5,252,643, DE-A-4316611, DE-A-4316622, DE-A-4316876, EP-A-0589839 and EP-A-0591102; 3-[4-(2-acetoxy-ethoxy)phenyl]-5,7-di-tert-butyl-benzofuran-2-one; 5,7-di-tert-butyl-3-[4-(2-stearoyloxyethoxy)-phenyl] benzofuran-2-one; 3,3'-bis[5,7-di-tert-butyl-3-(4-[2-hydroxyethoxy]phenyl)benzofuran-2-one]; 5,7-di-tert-butyl-3-(4-ethoxyphenyl)benzofuran-2-one; 3-(4-acetoxy-3,5-dimethylphenyl)-5,7-di-tert-butyl-benzofuran-2-one; 3-(3,5-dimethyl-4-pivaloyloxyphenyl)-5,7-di-tert-butyl-benzofuran-2-one; and 5,7-di-tert-butyl-3-(3,4-dimethylphenyl)-3H-benzofuran-2-one.

The trisaryl-1,3,5-triazines of the present invention can also be employed in multilayer systems. In such systems, a polymer composition having from about 0.1 to about 20% by weight and preferably a relatively high content of novel stabilizer, for example, about 5–15% by weight, is applied in a thin film (e.g., about 5–500 μm thick and, preferably, about 10–100 μm thick) to a shaped article made from a polymer containing little or no ultraviolet stabilizers. Such composition may be applied at the same time as the shaping of the base structure, for example by coextrusion in a manner analagous to that described in U.S. Pat. No. 4,948,666 (incorporated by reference herein for all purposes as if fully set forth). Alternatively, application can also be made to the ready-formed base structure, for example by lamination with a film or by coating with a solution. The outer layer or layers of the finished article have the function of a UV filter, which protects the interior of the article from UV light. The outer layer preferably contains about 0.1 to about 20%, preferably about 1 to about 15%, and most preferably about 2 to about 10% by weight of the outer layer composition, of at least one of the present trisaryl-1,3,5-triazine compounds of the present invention of the formulas (I), (II), or (III).

The polymers stabilized in this way are notable for high weathering resistance, especially for high resistance to UV light. This enables them to retain their mechanical properties, and their color surface properties such as gloss and distinctness of image, for a long time even when used outside. Moreover, due to the bondable nature of the presently claimed triazine compounds, migration of these UV absorbers between the layers of the multi-layer coatings can, under the appropriate circumstances, be minimized.

In another embodiment of the present invention, the novel mixtures comprising compounds of the formulas (I), (II), or (III) can be used as stabilizers for coatings, for example for paints such as disclosed in numerous of the previously incorporated references (see, e.g., U.S. Pat. No. 4,619,956, U.S. Pat. No. 4,740,542, U.S. Pat. No. 4,826,978, U.S. Pat. No. 4,962,142, U.S. Pat. No. 5,106,891, U.S. Pat. No. 5,198,498, U.S. Pat. No. 5,298,067, U.S. Pat. No. 5,322,868, U.S. Pat. No. 5,354,794, U.S. Pat. No. 5,369,140, U.S. Pat. No. 5,420,204, U.S. Pat. No. 5,461,151, U.S. Pat. No. 5,476,937, EP-0434608 and EP-A-0444323). Of particular interest are coatings and paints for the automobile industry. The invention therefore also relates to those compositions which are film-forming binders for coatings.

Such novel coating compositions comprise about 0.01 to about 20%, preferably about 0.01 to about 10%, and more preferably about 0.02 to about 5% by weight of the binder of the coating composition of the trisaryl-1,3,5-triazines of the present invention.

Multilayer systems are possible here as well (such as electrocoat/basecoat/clearcoat systems), where the concentration of the novel stabilizer in one or more of the layers, and typically the outer layer such as the clearcoat, can be relatively high, for example from about 0.01 to about 20%, preferably about 0.01 to about 10%, and more preferably about 0.02 to about 5% by weight of binder.

The use of the novel stabilizer in coatings is accompanied by the additional advantage that it prevents delamination, i.e. the flaking-off of the coating from the substrate. This advantage is particularly important in the case of metallic substrates, including multilayer systems on metallic substrates, and particularly epoxy e-coated metallic substrates.

The binder can in principle be any binder which is customary in industry, for example those described in Ullmann's Encyclopedia of Industrial Chemistry, 5th Edition, Vol. A18, pp. 368–426, VCH Verlagsgesellschaft, Weinheim 1991 which is incorporated herein by reference. In general, it is a film-forming binder based on a thermoplastic or curable resin, predominantly on a curable resin. Examples of thermoplastic binders include acrylics, polyesters, polyurethanes and PVC plastisols. Examples of curable binders include functional alkyd, acrylic, polyester, phenolic, melamine, epoxy and polyurethane resins and mixtures thereof.

Such curable binders can be an ambient curable or a thermosetting binder. Further, in some systems it may be advantageous to add a curing catalyst to such systems. Suitable catalysts which accelerate curing of the binder are described, for example, in Ullmann's Encyclopedia of Industrial Chemistry, 5th Edition, Vol. A18, p. 469, VCH Verlagsgesellschaft, Weinheim 1991 which is incorporated herein by reference. Preferred binders include those which comprise a functional acrylate resin and a crosslinking agent.

A wide variety of binders may be employed in such coating systems. Examples of suitable coating compositions containing specific binders include but are not limited to:

1. paints based on ambient curable or thermosetting alkyd, acrylate, polyester, epoxy or melamine resins or mixtures of such resins, if desired with addition of a curing catalyst;
2. two-component polyurethane paints based on hydroxyl-containing acrylate, polyester or polyether resins and aliphatic or aromatic isocyanates, isocyanurates or polyisocyanates;
3. one-component polyurethane paints based on blocked isocyanates, isocyanurates or polyisocyanates which are deblocked during baking;
4. two-component paints based on (poly)ketimines and aliphatic or aromatic isocyanates, isocyanurates or polyisocyanates;
5. two-component paints based on (poly)ketimines and an unsaturated acrylate resin or a polyacetoacetate resin or a methacrylamidoglycolate methyl ester;
6. two-component paints based on carboxyl- or amino-containing polyacrylates and polyepoxides;
7. two-component paints based on acrylate resins containing anhydride groups and on a polyhydroxy or polyamino component;
8. two-component paints based on (poly)oxazolines and acrylate resins containing anhydride groups, or unsaturated acrylate resins, or aliphatic or aromatic isocyanates, isocyanurates or polyisocyanates;
9. two-component paints based on unsaturated polyacrylates and polymalonates;
10. thermoplastic polyacrylate paints based on thermoplastic acrylate resins or externally crosslinking acrylate resins in combination with etherified melamine resins;
11. paint systems based on siloxane-modified or fluorine-modified acrylate resins.

In addition to the binder and trisaryl-1,3,5-triazines of the present invention, the coating composition according to the invention preferably further comprises one or more additional ultraviolet light absorbers, including but not limited to those specifically listed above in section b. The additional UV absorbers may be, for example, another tris-aryl-1,3,5-triazine, a 2-hydroxyphenyl-2H-benzotriazole, a 2-hydroxybenzophenone, an ester of an unsubstituted benzoic acid, an acrylate, an oxamide (oxanilide), or any combination of the above. Preferably, the additional UV absorber is a 2-hydroxyphenyl-2H-benzotriazole and the weight ratio of benzotriazole to triazine is 4:1 to 1:4. More preferably, the weight ratio of benzotriazole to triazine is 2:1 to 1:2.

To achieve maximum light stability, it is of particular interest to add sterically hindered amines, examples of which are set out in the above-mentioned section b(vi). The invention therefore also relates to a coating composition which, in addition to the binder, the novel trisaryl-1,3,5-triazines and, optionally, additional UV absorbers, comprises a light stabilizer of the sterically hindered amine type. The sterically hindered amine is employed in an amount of about 0.01 to 5% by weight based on the weight of the solid binder, preferably about 0.02 to 2% by weight.

One specific example of such a sterically hindered amine is a 2,2,6,6-tetramethyl piperazinone containing at least one group of the formula:

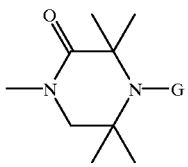

in which G is, for example, hydrogen, hydroxyl, alkyl (such as methyl), alkoxy (such as methoxy) or acyl.

More preferably the stabilizer is a 2,2,6,6-tetraalkylpiperidine derivative containing at least one group of the formula:

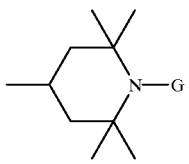

in which G is, for example, hydrogen, hydroxyl, alkyl (such as methyl), alkoxy (such as methoxy) or acyl.

Examples of tetraalkylpiperidine derivatives which can be used in combination with the present trisaryl-1,3,5-triazine compounds are given in U.S. Pat. No. 4,314,933, U.S. Pat. No. 4,344,876, U.S. Pat. No. 4,426,471, U.S. Pat. No. 4,426,472, U.S. Pat. No. 4,619,956, U.S. Pat. No. 5,004,770, U.S. Pat. No. 5,006,577, U.S. Pat. No. 5,064,883, U.S. Pat. No. 5,112,890, U.S. Pat. No. 5,124,378, U.S. Pat. No. 5,106,891, U.S. Pat. No. 5,204,473, U.S. Pat. No. 5,461,151 and EP-A-0434608 which (to the extent not already done so) are incorporated by reference herein for all purposes as if fully set forth. It is particularly expedient to employ the following tetraalkylpiperidine derivatives, as well as their N-alkyl, N-acyl, N-hydroxyl and N-alkoxy analogs (where not already included in the following list):

bis(2,2,6,6-tetramethylpiperid-4-yl) succinate, bis(2,2,6,6-tetramethylpiperid-4-yl) sebacate, bis(1,2,2,6,6-pentamethylpiperid-4-yl) sebacate, di(1,2,2,6,6-pentamethylpiperid-4-yl) butyl-(3,5-di-tert-butyl-4-hydroxybenzyl)malonate, bis(1-octyloxy-2,2,6,6-tetramethylpiperid-4-yl) sebacate, tetra(2,2,6,6-tetramethylpiperid-4-yl) butane-1,2,3,4-tetracarboxylate, tetra(1,2,2,6,6-pentamethylpiperid-4-yl) butane-1,2,3,4-tetracarboxylate, 2,2,4,4-tetramethyl-7-oxa-3,20-diaza-21-oxo-dispiro[5.1.11.2] heneicosane, and 8-acetyl-3-dodecyl-1,3,8-triaza-7,7,9,9-tetramethylspiro[4.5]decane-2,4-dione. Commercially available examples of these and other tetraalkylpipieridine derviatives include SANDUVOR® 3050, 3052, 3055, 3056, 3058, PR-31 and PR-32 (Clariant Corp.); TINUVIN® 079L, 123, 144, 292, 440L and 622LD (Ciba Specialty Chemicals); CHIMASORB® 119 (Ciba Specialty Chemicals); and CYAGARD® UV-3853, UV-500 and UV-516 (Cytec Industries Inc.).

Apart from the binder, the trisaryl-1,3,5-triazine, and, if used, the additional ultraviolet light absorber or stabilizer, the coating composition can also comprise further components, examples being solvents, pigments, dyes, plasticizers, stabilizers, thixotropic agents, drying catalysts and/or leveling agents. Examples of possible components are those described in many of the previously incorporated references as well as Ullmann's Encyclopedia of Industrial Chemistry, 5th Edition, Vol. A18, pp. 429–471, VCH Verlagsgesellschaft, Weinheim 1991; and Calbo, Leonard J., ed., Handbook of Coatings Additives, New York:Marcel Dekker (1987).

Possible drying catalysts or curing catalysts are, for example, organometallic compounds, amines, amino-containing resins and/or phosphines.

Examples of organometallic compounds are metal carboxylates, especially those of the metals Pb, Mn, Co, Zn, Zr or Cu, or metal chelates, especially those of the metal Al, Ti or Zr, or organometallic compounds such as organotin compounds, for example. Examples of metal carboxylates are the stearates of Pb, Mn or Zn, the octoates of Co, Zn or Cu, the naphthenates of Mn and Co or the corresponding linoleates, resinates or tallates. Examples of metal chelates are the aluminum, titanium or zirconium chelates of acetylacetone, ethyl acetylacetate, salicylaldehyde, salicylaldoxime, o-hydroxyacetophenone or ethyl trifluoroacetylacetate and the alkoxides of these metals. Examples of organotin compounds are dibutyltin oxide, dibutyltin dilaurate or dibutyltin dioctoate.

Examples of amine drying or curing catalysts are, in particular, tertiary amines, for example tributylamine, triethanolamine, N-methyldiethanolamine, N-dimethylethanolamine, N-ethylmorpholine, N-methylmorpholine or diazabicyclooctane (triethylenediamine) and salts thereof. Further examples are quaternary ammonium salts, for example trimethylbenzylammonium chloride. Amino-containing resins are simultaneously binder and curing catalyst. Examples thereof are amino-containing acrylate copolymers.

The curing catalyst used can also be a phosphine, for example triphenylphosphine.

Another type of curing catalyst is a peroxide which can be used, for example, to cure a gel coating for a fiberglass article.

The novel coating compositions can also be radiation-curable coating compositions. In this case, the binder essentially comprises monomeric or oligomeric compounds containing ethylenically unsaturated bonds, which after application are cured by actinic radiation, i.e. converted into a crosslinked, high molecular weight form. Where the system is UV-curing, it generally contains a photoinitiator as well. Corresponding systems are described in the above-mentioned publication Ullmann's Encyclopedia of Industrial Chemistry, 5th Edition, Vol. A18, pages 451–453. In radiation-curable coating compositions, the novel stabilizers can also be employed without the addition of sterically hindered amines.

The novel coating compositions according to the invention can be applied to any desired substrates, for example to metal, wood, plastic, fiberglass or ceramic materials. The coating compositions can be pigmented mono-coats or multi-layer (primer/basecoat/clearcoat) systems typical of automotive finishes. In the latter case, the novel coating composition can be used for either the base coat, or clear coat, or for both layers. If the topcoat of an automotive finish comprises two layers, of which the lower layer is pigmented and the upper layer is not pigmented, the novel coating composition can be used for either the upper or the lower layer or for both layers, but preferably for the upper topcoat layer.

The novel coating compositions can be applied to the substrates by the customary methods, for example by brushing, spraying, pouring, dipping or electrophoresis; see also Ullmann's Encyclopedia of Industrial Chemistry, 5th Edition, Vol. A18, pp. 491–500.

Depending on the binder system, the coatings can be cured at room temperature or by heating. Thermosetting coatings are preferably cured at 50–150° C. and, in the case of powder coatings, even at higher temperatures.

The coatings obtained in accordance with the invention have excellent resistance to the damaging effects of light, oxygen and heat; particular mention should be made of the good light stability and weathering resistance of the coatings thus obtained, for example paints.

The invention therefore also relates to a coating, in particular a paint, which has been stabilized against the damaging effects of light, oxygen and heat by a content of the compound of the formula (I), (II) or (III) according to the invention. The paint can be a pigmented mono-coat which comprises a film-forming binder and an organic pigment or dye, an inorganic pigment, a metallic pigment, or a mixture thereof. The paint may also be a composition which comprises a primer in adhesion to a metal or plastic substrate; a pigmented basecoat that is in adhesion to the primer and which comprises a film-forming binder and an organic pigment or dye, an inorganic pigment, a metallic pigment, or a mixture thereof; and a clear coat that is in adhesion to the base coat and which comprises a film-forming binder and optionally a transparent pigment. One especially preferred use is a paint which is a clear topcoat for automobile original equipment manufacture (OEM) and/or refinish applications.

The invention furthermore relates to a process for stabilizing a coating based on polymers against damage by light, oxygen and/or heat, which comprises mixing with the coating composition a mixture comprising a trisaryl-1,3,5-triazine of the present invention, and to the use of mixtures comprising such trisaryl-1,3,5-triazine compounds in coating compositions as stabilizers against damage by light, oxygen and/or heat.

The coating compositions can comprise an organic solvent or solvent mixture in which the binder is soluble. The coating composition can otherwise be an aqueous solution or dispersion. The vehicle can also be a mixture of organic solvent and water. The coating composition maybe a high-solids paint or can be solvent-free (e.g. a powder coating material).

The pigments can be inorganic, organic or metallic pigments. The novel coating compositions preferably contain no pigments and are used as a clearcoat.

Likewise preferred is the use of the coating composition as a topcoat for applications in the automobile industry, especially as a pigmented or unpigmented topcoat of the paint finish. Its use for underlying coats, however, is also possible.

The triazines of this invention may be applied topically by polishing a surface with a composition comprising the triazines and an inert carrier such as solvent, petroleum jelly, silicone oil in water emulsions, or automotive paint wax, e.g. Carnauba wax. These topical treatment compositions may be used to stabilize coating films, fabrics, leather, vinyl and other plastics and wood.

Preference is also given to the use of the novel trisaryl-1,3,5-triazine compounds in photographic materials as stabilizer against damage by light, especially by UV light. The invention therefore also relates to a photographic material comprising the present trisaryl-1,3,5-triazine compounds.

The compounds according to the invention can be used for photosensitive materials of all kinds. For example, they can be employed for color paper, color reversal paper, direct-positive color material, color negative film, color positive film, color reversal film and other materials. They are preferably used, inter alia, for photosensitive color material which comprises a reversal substrate or which forms positives.

Furthermore, the novel compounds can be combined with other UV absorbers, especially those which are dispersible in aqueous gelatin, for example with Hydroxyphenyl] benzotriazole (cf. for example U.S. Pat. No. 4,853,471, U.S. Pat. No. 4,973,702, U.S. Pat. No. 4,921,966 and U.S. Pat. No. 4,973,701), benzophenones, oxanilides, cyanoacrylates, salicylates, or acrylonitriles or thiazolines. In this context it is advantageous to employ these further, oil-dissolved UV absorbers in the photographic material in layers other than those comprising the novel UV absorbers.

In particular, it is possible successfully to stabilize photographic materials similar to those described in U.S. Pat. No. 4,518,686.

The invention therefore additionally relates to a photographic material comprising, on support, a blue-sensitive, a green-sensitive and/or a red-sensitive silver-halide emulsion layer and, if desired, a protective layer, with a layer comprising a UV absorber being arranged above the uppermost silver-halide emulsion layer, wherein the UV absorber is a trisaryl-1,3,5-triazine compound of the present invention.

Preference is additionally given to photographic materials which have a layer comprising a compound of the formula (I), (II) or (III) above the uppermost silver-halide emulsion layer and/or between the green- and red-sensitive silver-halide emulsion layers.

Furthermore, it may be advantageous for all or some of the layers which can comprise a UV absorber to have a UV absorber mixture and/or a further UV absorber which is dispersible in aqueous gelatin, but a compound of the formula (I), (II) or (III) must be present at least in one layer.

The novel material preferably has gelatin interlayers between the silver-halide emulsion layers.

Preference is given to photographic materials in which the silver halide in the blue-sensitive, green-sensitive and/or red-sensitive layer is silver chloride bromide comprising at least 90 mol % of silver chloride.

The compounds of the formula (I), (II) or (III) which are used in accordance with the invention can be incorporated, alone or together with the color coupler and, if used, further additives, into the color photographic materials by dissolving the compounds beforehand in high-boiling organic solvents. It is preferred to use solvents which boil at higher than 160° C. Typical examples of such solvents are the esters of phthalic acid, phosphoric acid, citric acid, benzoic acid or of fatty acids and also alkylamides and phenols.

Preferred color couplers for use in the compositions of the invention, examples of such compounds, further additives such as color cast inhibitors, DIR couplers and further light stabilizers, such as UV absorbers, phenols, phosphorus (III) compounds, organometallic complexes, hydroquinones and hydroquinone ethers, and more precise details on the structure of various photographic materials, can be found, for example, in the publications EP-A-0531258 and EP-A-0520938 and in the literature cited therein.

The trisaryl-1,3,5-triazine compounds of the formula (I), (II) or (III) are suitable for the photochemical stabilization of undyed, dyed or printed fiber materials comprising for example, silk, leather, wool, polyamide or polyurethanes and especially cellulose-containing fiber materials of all kinds. Examples of such fiber materials are the natural cellulose fibers, such as cotton, linen, jute and hemp and also viscose staple fiber and regenerated cellulose. Preferred textile fiber materials are those of cotton. The triazine compounds of the present invention are also suitable for the photochemical stabilization of hydroxyl-containing fibers in blend fabrics, for example blends of cotton with polyester fibers or polyamide fibers. A further preferred area of application relates to the blocking or reduction of the UV radiation which passes through the above-mentioned textile materials (UV cutting) and the heightened sun protection which textile materials finished with a novel compound offer to the human skin.

To this end, one or a number of different compounds of the formula (I), (II) or (III) are applied to the textile fiber material by one of the customary dyeing methods, advantageously in a quantity of 0.01 to 5% by weight, preferably 0.1 to 3% by weight and, in particular, from 0.25 to 2% by weight, based on the weight of the fiber material.

The present trisaryl-1,3,5-triazine compounds can be applied to the fiber material in various ways and fixed on the fiber, especially in the form of aqueous dispersions or printing pastes.

The textile fiber materials finished with the novel compounds of the formula (I), (II) or (III) possess improved protection against photochemical breakdown of the fiber and yellowing phenomena and, in the case of dyed fiber material, are of enhanced (hot) light fastness. Particular emphasis should be drawn to the greatly improved photoprotective effect of the treated textile fiber material and, in particular, the good protective effect with respect to short-wave UV-B rays. This is manifested by the fact that the textile fiber material finished with a trisaryl-1,3,5-triazine compound has, relative to untreated fabric, a greatly increased sun protection factor (SPF).

The sun protection factor is defined as the quotient of the dose of UV radiation which damages protected skin to that which damages unprotected skin. Accordingly, a sun protection factor is also a measure of the extent to which untreated fiber materials and fiber materials treated with a novel compound of the formula (I), (II) or (III) are permeable to UV radiation. The determination of the sun protection factor of textile fiber materials is explained, for example, in WO94/04515 or in J. Soc. Cosmet. Chem. 40, 127–133 (1989) and can be carried out analogously thereto.

Yet another use of the UV absorbers according to the invention is in the stabilization of intra-ocular and contact lenses.

The UV absorbers according to the invention are suitable, furthermore, as photoprotective agents in cosmetic preparations. The invention additionally relates, therefore, to a cosmetic preparation comprising at least one such trisaryl-1,3,5-triazine compound and cosmetically acceptable carriers or auxiliaries.

The novel cosmetic composition contains from 0.1 to 15% by weight, preferably from 0.5 to 10% by weight, based on the overall weight of the composition, of a trisaryl-1,3,5-triazine UV absorber and a cosmetically acceptable auxiliary.

The cosmetic composition can be prepared by physically mixing the novel UV absorber with the auxiliary by means of customary methods, for example by simply stirring together the two materials.

The cosmetic preparation according to the invention can be formulated as a water-in-oil or oil-in-water emulsion, as an oil-in-oil alcohol lotion, as a vesicular dispersion of an ionic or nonionic amphiphilic lipid, as a gel, solid stick or as an aerosol formulation.

As a water-in-oil or oil-in-water emulsion, the cosmetically acceptable auxiliary preferably contains from 5 to 50% of an oily phase, from 5 to 20% of an emulsifier and from 30 to 90% water. The oil phase mentioned can comprise any oil which is suitable for cosmetic formulations, for example one or more hydrocarbon oils, a wax, a natural oil, a silicone oil, a fatty acid ester or a fatty alcohol. Preferred mono- or polyols are ethanol, isopropanol, propylene glycol, hexylene glycol, glycerol and sorbitol.

For the cosmetic formulations according to the invention it is possible to use any conventionally employed emulsifier, for example one or more ethoxylated esters of naturally occurring derivatives, for example polyethoxylated esters of hydrogenated castor oil; or a silicone oil emulsifier such as silicone polyol; an unmodified or ethoxylated fatty acid soap; an ethoxylated fatty alcohol; an unmodified or ethoxylated sorbitan ester; an ethoxylated fatty acid; or an ethoxylated glyceride.

The cosmetic formulation can also comprise further components, for example emollients, emulsion stabilizers, skin moisteners, tanning accelerators, thickeners such as xanthan, moisture retention agents such as glycerol, preservatives, or fragrances and colorants.

The novel cosmetic formulations are notable for good protection of human skin against the damaging effect of sunlight while at the same time providing for reliable tanning of the skin.

The invention will now be illustrated by the following examples. The examples are not intended to be limiting of the scope of the present invention. In conjunction with the general and detailed descriptions above, the examples provide further understanding of the present invention.

EXAMPLES

Preparation of Compound A

2-[2-hydroxy-4-(acetoacetyloxyethyloxy)phenyl]-4,6-bis(2,4-dimethylphenyl)-1,3,5-triazine (Compound A) was synthesized using the following reaction scheme:

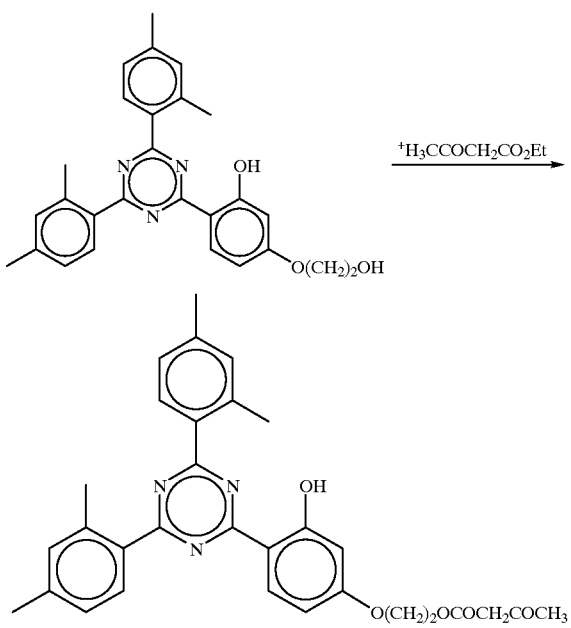

The following were added, from first to last, to a 2 neck round bottom flask equipped with a magnetic stirring bar, a reflux condenser, an argon inlet and a glass stopper:

4.41 g of 2-[2-hydroxy-4-(hydroxyethyloxy)phenyl]-4,6-bis(2,4-dimethylphenyl)-1,3,5-triazine, 5.0 ml of ethyl acetoacetate, 20.0 ml of xylene, and 60 mg of dimethylaminopyridine ("DMAP") as catalyst.

The reaction mixture was heated to reflux for 16 hours, then allowed to cool to room temperature and concentrated under reduced pressure to remove volatiles. The residue was purified by silica gel column chromatography to give 4.46 g of a product determined to be Compound A by $^1$H NMR, $^{13}$C NMR and mass spectroscopy.

Preparation of Compound B

2-[2-hydroxy-4-(acetoacetyloxyhexyloxy)phenyl]-4,6-bis(2,4-dimethylphenyl)-1,3,5-triazine (Compound B) was synthesized using the following reaction scheme:

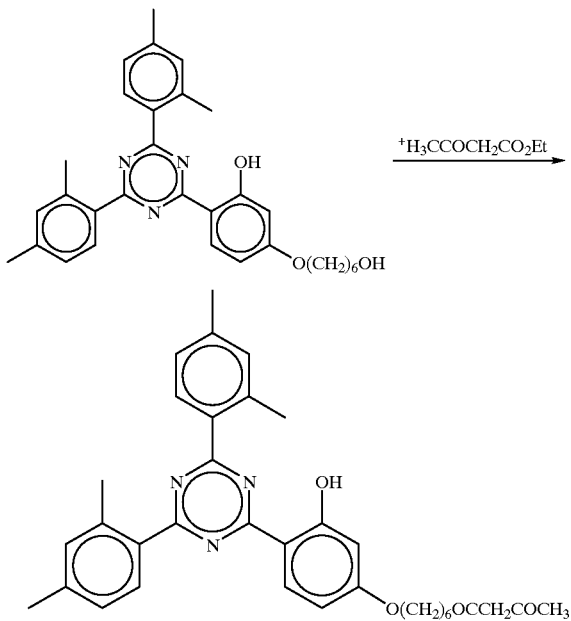

The following were added, from first to last, to a 2 neck round bottom flask equipped with a magnetic stirring bar, a reflux condenser, an argon inlet and a glass stopper:

1.5 g of 2-[2-hydroxy-4-(hydroxyhexyloxy)phenyl]-4,6-bis(2,4-dimethylphenyl)-1,3,5-triazine, 1.5 ml of ethyl acetoacetate, 10 ml of xylene, and 18 mg of DMAP as catalyst.

The reaction mixture was heated to reflux for 6 hours, then allowed to cool to room temperature and concentrated under reduced pressure to remove volatiles. The residue was purified by silica gel column chromatography to give 1.55 g of a product determined to be Compound B by $^1$H NMR, $^{13}$C NMR and mass spectroscopy.

Preparation of Compound C

2-[2-hydroxy-4-((N-ethyl-N-acetoacetyloxyethyl)methanamidooxy)phenyl]-4,6-bis(2,4-dimethylphenyl)-1,3,5-triazine (Compound C) was synthesized using the following reaction scheme:

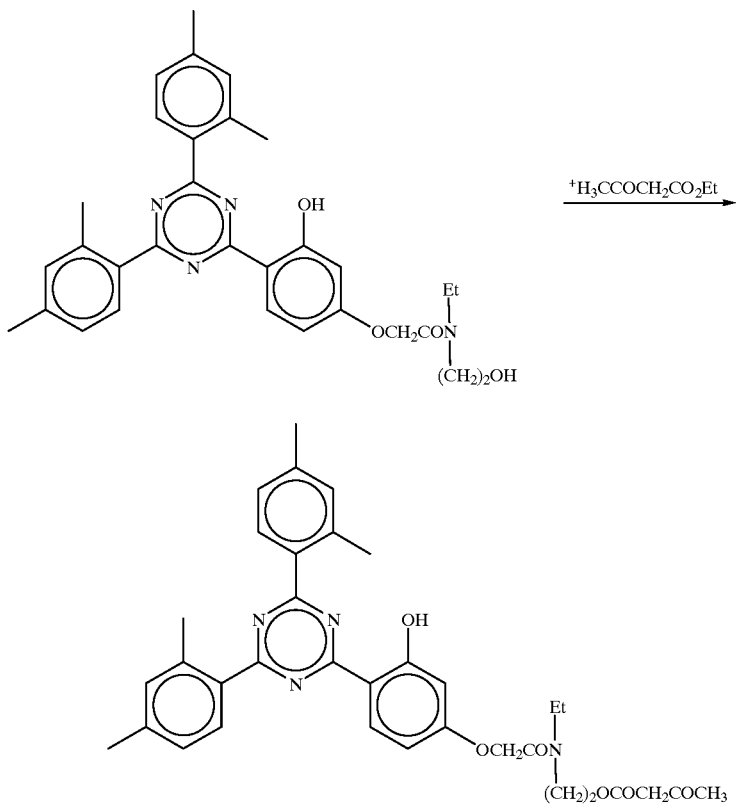

The following were added, from first to last, to a 2 neck round bottom flask equipped with a magnetic stirring bar, a reflux condenser, an argon inlet and a glass stopper:

20 g of 2-[2-hydroxy-4-((N-ethyl-N-hydroxyethyl) methanamidooxy)phenyl]-4,6-bis(2,4-dimethylphenyl)-1,3,5-triazine, 19.8 ml of ethyl acetoacetate, 150 ml of xylene, and 230 mg of DMAP as catalyst.

The reaction mixture was heated to reflux for 3 hours, then allowed to cool to room temperature and concentrated under reduced pressure to remove volatiles. The residue was purified by silica gel column chromatography to give 24.67 g of a product determined to be Compound C by $^1$H NMR, $^{13}$C NMR and mass spectroscopy.

Preparation of Compound D

2-[2-hydroxy-4-((N-acetoacetyloxyethyl) methanamidooxy)phenyl]-4,6-bis(2,4-dimethylphenyl)-1,3,5-triazine (Compound D) was synthesized using the following reaction scheme:

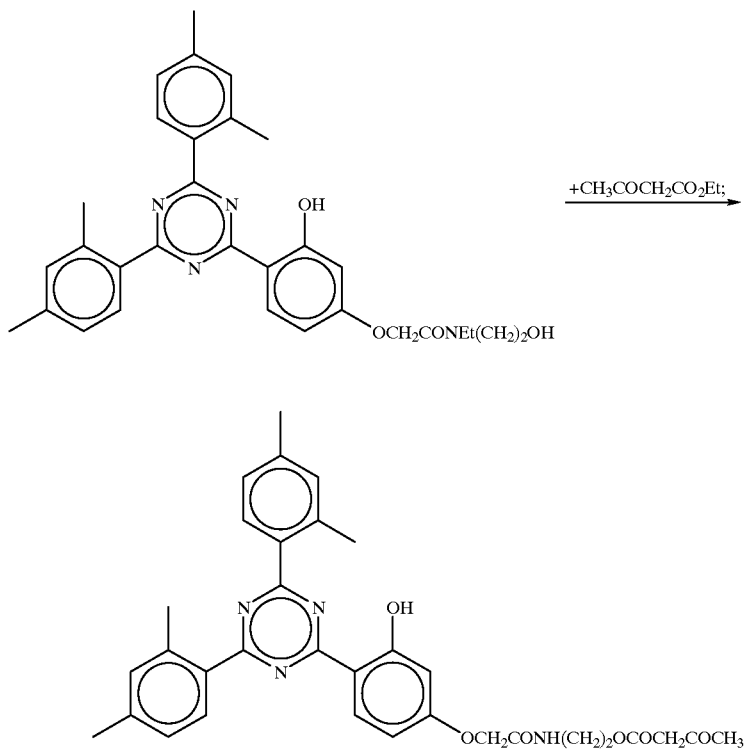

The following were added, from first to last, to a 500-mL round bottom flask equipped with a magnetic stirring bar, a reflux condenser, and a nitrogen inlet:

20 g of 2-[2-hydroxy-4-((N-hydroxyethyl) methanamidooxy)phenyl]-4,6-bis(2,4-dimethylphenyl)-1,3,5-triazine 20.8 g of ethyl acetoacetate 250 mL of xylenes 240 mg of DMAP as catalyst.

The reaction mixture was heated to reflux. After 3 hr., TLC analysis indicated that the triazine starting material was completely consumed. The reaction mixture was diluted with hexanes and allowed to cool to room temperature. The resulting solids were collected by filtration, washed with hexanes and allowed to air dry to give 23 g of a product determined to be Compound D by $^1$H-NMR spectroscopy.

Example 1 Bondability of Compound A

A mixture of 780 mg of CYMEL® 303 (a highly methylated melamine-formaldehyde resin of Cytec Industries Inc., West Paterson, N.J.), 1.05 g of Compound A, 40 mg p-toluene sulfonic acid (acid catalyst), and toluene was heated at reflux for 4 hours. A thin layer chromatography analysis of the reaction mixture revealed that Compound A had completely reacted with the CYMEL® 303. Accordingly, one of ordinary skill in the art would recognize that the acetoacetate functionalized trisaryl-1,3,5-triazine is a bondable material.

Example 2 Bonding of Compound B to Acrylic/Melamine Resin Matrix

Compound B was investigated to determine whether it forms a chemical bond with the acrylic/melamine resin matrix during cure. For this purpose, it was added to a clearcoat formulation and coated onto a plastic substrate, as described below. Non-bondable UV absorbers readily migrate from clearcoats into plastic substrates upon curing the coating. An absorber which bonds to the matrix should not migrate into the plastic substrate to any significant extent.

The acrylic/melamine resin formulation utilized was as follows:

40.6 g JONCRYL® 510 acrylic resin (S.C. Johnson & Son, Inc., Racine, Wis.)

17.5 g CYMEL® 303 crosslinker (Cytec Industries Inc., West Paterson, N.J.)

0.52 g CYCAT® 4040 catalyst (Cytec Industries Inc., West Paterson, N.J.)

10.0 g n-Butanol 0.50 g DC 57 flow control agent 8.0 g Xylene.

To this formulation was added 3% of Compound B based on total resin solids.

The resulting coating was drawn onto plastic RIM substrates (Dow SPECTRIM® 50) using a #58 cator rod and cured for 30 minutes at 135° C. After cure, the coating and part of the substrate were microtomed into 10 μm thick slices parallel to the coating surface. The microtome was a Reichert-Jung Polycut E instrument. Each microtomed slice was mounted between two microscope slides and its UV absorption spectrum measured using a Perkin-Elmer Lambda 2 spectrophotometer. The absorbance per micrometer sample thickness was determined at the prominent 340 nm absorption band intrinsic to this UVA.

The results of the UV analysis were plotted as function of depth. The original coating surface in contact with the atmosphere is located at 0 μm. The coating/substrate interface was at about 70 μm below the surface. The total microtomed depth was about 130 μm. The plotted curve showed a steep drop of the absorbance near the coating/substrate interface, indicating that most of the Compound B molecules remained in the coating, and only minor amounts migrated through the interface into the plastic substrate. By measuring the area under the curve, the quantity of Compound B remaining in the coatings and the fraction that migrated into the substrates were estimated. The result is that about 85% of the added Compound B remained in the coating, with only about 15% migrating into the substrate. For comparison, CYAGARD® UV 1164L (a non-bondable triazine UV absorber available from Cytec Industries Inc.) was found to migrate into RIM substrates. Under identical experimental conditions (30 minutes cure at 135° C.), 63% of the added non-bondable triazine UVA migrated into the substrate and only 37% was left in the coating.

Example 3 Bonding of Compound B to Polyurethane Resin Matrix

Bonding of Compound B in a solvent based polyurethane coating was confirmed by a second experiment. The solvent based polyurethane coating used had the following formula:

103 g JONCRYL® CDX-588 acrylic resin (68% solids) (S.C. Johnson & Son, Inc., Racine, Wis.)

33 g DESMODUR N-3390 crosslinker (90% solids) (Bayer Corp., Pittsburgh, Pa.)

59 g 1:1:1 xylene:MAK:PM Acetate solvent mix 5 g T-12 catalyst.

Compound B was added to this formulation at the 2% level.

The coating was drawn onto a block copoly(ester-ether) plastic substrate (HYTREL® DYM 100, available from E.I. duPont de Nemours and Company) used for automotive applications, with a #58 cator rod. After cure at 120° C. for 30 minutes, the coating and part of the substrate were microtomed and the microtomed slices extracted using supercritical fluid extraction. The extracts were analyzed for Compound B using HPLC. No Compound A was detected in the slices cut from the substrate, and only 0.48% was found in the coating. This indicates that Compound B was chemically bonded to the coating resin matrix.

Example 4 Accelerated Weathering Testing of Clear Coatings

Formation of Clear Coatings

Compounds A and B were formulated in clear coatings which were applied to panels for accelerated weathering testing as follows. Compound A or B (2% based on total resin solids) and/or SANDUVOR® S-3055 HALS-type stabilizer (1% based on total resin solids) were predissolved in the solvent mixture (to a 5–10% solids level) and added to the clear acrylic urethane formulation given in Table 1 below. Components I and II were mixed just before use. Cold roll steel panels measuring 4"×12" and precoated with an electro-coat primer ED5050A and a white polyester acrylic melamine base-coat #542AB839, obtained from ACT Laboratories, Inc. (Hillsdale, Mich.) were coated with the clear coating formulations of Table 1. The draw-down technique, using WC-60 WireCators™ (Leneta Co., Ho-Ho-Kus, N.J.), was used to apply the clear coat to the pre-coated panels. The clear coats were allowed to flash for 10 min at ambient temperature and cured for 30 min at 135° C.

TABLE 1

Acrylic Urethane Clear Coat Formulation

| Raw Material | Supplier | Amount |
| --- | --- | --- |
| Component I Composition | | |
| Acrylic Resin: JONCRYL® CDX-588 (70% Solids) | S. C. Johnson & Son, Inc., Racine, WI | 100 parts |
| Catalyst Solution | | 5 parts |
| Solvent Mixture | | 45 parts |
| Triazine UV Absorber | | 1 or 2 parts[a] |
| SANDUVOR® S-3055 (HALS type stabilizer) | Clariant Corp., Charlotte, NC | 1 part[b] |
| Component II Composition | | |
| Isocyanate: DESMODUR® N-3390 (90% Solids) | Miles, Inc., Pittsburgh, PA | 33 parts |
| Solvent Mixture | | 17 parts |
| Catalyst Solution Composition: (2% Solids in Catalyst Solution:) | | |
| Dibutyltin Dilaurate: T-12 | Air Products, Allentown, PA | 1 part |
| Acetic Acid | | 4 parts |
| Propylene Glycol Methyl Ether Acetate (PM Acetate) | | 45 parts |
| Solvent Mixture: | | |
| Xylenes | | 1 part |
| PM Acetate | | 1 part |
| Methyl Amyl Ketone (MAK) | | 1 part |

[a]Amount for 2% based on total resin solids
[b]Optional - when utilized the amount for 1% based on total resin solids Accelerated weathering was carried out on the clear coating formulations using (1) a QUV device equipped with UVB-313 fluorescent bulbs, and (2) an Atlas Ci65 WeatherOmeter equipped with xenon arc lamps. In (1), the coated panels were subjected to accelerated weathering under alternate cycles of (i) UV light at 70° C. for 8 hours and (ii) condensation with no UV light at 50° C. for 4 hours (ASTM G53, GM cycle). In (2), the coated panels were subjected to accelerated weathering using the SAE J1960 automotive exterior test protocol. Specular properties such as gloss (20°, ASTMD523) and distinctness of image ("DOI") (Dorigon Meter D47R-6FT, Hunter Associate Laboratory) and yellowing ("Delta b") were measured as a function of weathering time.

The effect of Compounds A or B on gloss retention, DOI retention and yellowing under QUV exposure is given in Table 2. The effect of Compounds A or B in combination with S-3055 on gloss retention, DOI retention and yellowing under QUV exposure is given in Table 3. The effect of Compounds A or B on gloss retention, DOI retention and yellowing under xenon WeatherOmeter exposure is given in Table 4.

TABLE 2

QUV Weathering (UVA Alone)

| Hours Exposure | % Comp. A | % Comp. B | Gloss | DOI | b |
|---|---|---|---|---|---|
| 0 | — | — | 93.5 | 77.0 | 3.65 |
|  | 2 | — | 95.5 | 85.2 | 3.81 |
|  | — | 2 | 94.3 | 78.2 | 3.82 |

| Hours Exposure | % Comp. A | % Comp. B | % Gloss Retention | % DOI Retention | Delta b |
|---|---|---|---|---|---|
| 544 | — | — | 100.5 | 94.8 | 5.93 |
|  | 2 | — | 101.6 | 100.7 | 2.55 |
|  | — | 2 | 99.5 | 100.2 | 2.92 |
| 1047 | — | — | 101.4 | 97.1 | 8.81 |
|  | 2 | — | 101.9 | 102.6 | 3.47 |
|  | — | 2 | 100.2 | 100.7 | 3.89 |
| 1449 | — | — | 101.9 | 101.9 | 10.48 |
|  | 2 | — | 101.7 | 106.0 | 3.97 |
|  | — | 2 | 100.2 | 101.3 | 4.50 |
| 1984 | — | — | 98.4 | 101.4 | 11.01 |
|  | 2 | — | 100.1 | 104.7 | 4.48 |
|  | — | 2 | 98.2 | 100.5 | 4.89 |
| 2486 | — | — | 29.1 | 13.1 | 10.80 |
|  | 2 | — | 96.4 | 106.0 | 4.85 |
|  | — | 2 | 95.0 | 100.5 | 5.46 |
| 2989 | — | — | fail | fail | fail |
|  | 2 | — | 84.6 | 89.4 | 5.17 |
|  | — | 2 | 79.2 | 99.2 | 5.72 |

TABLE 3

QUV Weathering (UVA + HALS)

| Hours Exposure | % Comp. A | % Comp. B | % HALS | Gloss | DOI | b |
|---|---|---|---|---|---|---|
| 0 | — | — | 1 | 94.1 | 88.8 | 3.70 |
|  | 2 | — | 1 | 94.8 | 86.0 | 4.44 |
|  | — | 2 | 1 | 94.6 | 86.1 | 4.07 |

| Hours Exposure | % Comp. A | % Comp. B | % HALS | % Gloss Retention | % DOI Retention | Delta b |
|---|---|---|---|---|---|---|
| 544 | — | — | 1 | 100.7 | 101.1 | 2.94 |
|  | 2 | — | 1 | 100.8 | 101.0 | 0.86 |
|  | — | 2 | 1 | 101.0 | 100.9 | 1.26 |
| 1047 | — | — | 1 | 101.7 | 100.6 | 3.80 |
|  | 2 | — | 1 | 101.3 | 100.2 | 1.43 |
|  | — | 2 | 1 | 101.0 | 100.9 | 1.26 |
| 1449 | — | — | 1 | 101.1 | 101.2 | 4.47 |
|  | 2 | — | 1 | 101.3 | 101.2 | 1.65 |
|  | — | 2 | 1 | 101.7 | 102.0 | 2.03 |
| 1984 | — | — | 1 | 100.3 | 101.1 | 5.44 |
|  | 2 | — | 1 | 99.7 | 100.7 | 2.01 |
|  | — | 2 | 1 | 100.5 | 102.1 | 2.33 |
| 2486 | — | — | 1 | 97.4 | 99.0 | 6.89 |
|  | 2 | — | 1 | 97.6 | 100.9 | 2.27 |
|  | — | 2 | 1 | 98.4 | 102.3 | 2.64 |
| 2989 | — | — | 1 | 93.9 | 98.5 | 8.13 |
|  | 2 | — | 1 | 94.7 | 101.5 | 2.53 |
|  | — | 2 | 1 | 94.9 | 103.3 | 2.83 |
| 3467 | — | — | 1 | 39.7 | 13.5 | 7.72 |
|  | 2 | — | 1 | 98.9 | 101.7 | 2.78 |
|  | — | 2 | 1 | 98.7 | 101.5 | 3.06 |
| 3967 | — | — | 1 | 24.5 | 15.0 | 8.08 |
|  | 2 | — | 1 | 93.4 | 100.3 | 3.05 |
|  | — | 2 | 1 | 92.7 | 99.3 | 3.34 |
| 4443 | — | — | 1 | fail | fail | fail |
|  | 2 | — | 1 | 84.6 | 92.2 | 3.07 |
|  | — | 2 | 1 | 83.4 | 88.2 | 3.38 |

TABLE 4

Xenon Weathering (UVA Alone)

| Hours Exposure | % Comp. A | % Comp. B | Gloss | DOI | b |
|---|---|---|---|---|---|
| 0 | — | — | 93.1 | 77.5 | 3.70 |
|  | 2 | — | 94.7 | 90.2 | 4.32 |
|  | — | 2 | 94.5 | 86.4 | 4.09 |

| Hours Exposure | % Comp. A | % Comp. B | % Gloss Retention | % DOI Retention | Delta b |
|---|---|---|---|---|---|
| 1027 | — | — | 99.0 | 94.7 | 0.98 |
|  | 2 | — | 96.9 | 100.1 | 0.54 |
|  | — | 2 | 100.0 | 100.3 | 0.72 |
| 2000 | — | — | 97.7 | 94.6 | 1.35 |
|  | 2 | — | 97.4 | 100.4 | 0.88 |
|  | — | 2 | 100.0 | 100.8 | 1.07 |
| 2988 | — | — | 96.7 | 94.2 | 1.60 |
|  | 2 | — | 92.5 | 99.9 | 1.03 |
|  | — | 2 | 96.2 | 100.0 | 1.20 |
| 3998 | — | — | 79.9 | 74.8 | 1.98 |
|  | 2 | — | 90.9 | 99.3 | 1.30 |
|  | — | 2 | 95.4 | 96.4 | 1.47 |
| 5000 | — | — | 63.1 | 69.8 | 1.97 |
|  | 2 | — | 82.6 | 93.1 | 1.13 |
|  | — | 2 | 83.8 | 92.6 | 1.43 |
| 6012 | — | — | 51.9 | 56.0 | 2.44 |
|  | 2 | — | 76.0 | 89.1 | 1.47 |
|  | — | 2 | 80.5 | 102.1 | 1.66 |
| 6997 | — | — | 34.7 | 33.4 | 2.90 |
|  | 2 | — | 68.5 | 80.9 | 1.42 |
|  | — | 2 | 67.0 | 77.7 | 1.60 |
| 7998 | — | — | 12.6 | 17.2 | 6.50 |
|  | 2 | — | 57.0 | 69.4 | 1.70 |
|  | — | 2 | 56.9 | 65.2 | 1.95 |
| 8500 | — | — | fail | fail | fail |
|  | 2 | — | 56.4 | 63.1 | 1.74 |
|  | — | 2 | 59.9 | 57.2 | 1.88 |

Although the present invention is described with reference to certain preferred embodiments, it is apparent that modifications and variations thereof may be made by those skilled in the art without departing from the scope of this invention as defined by the appended claims.

What is claimed is:

1. A method of stabilizing a material which is subject to degradation by actinic radiation by incorporating into said material an amount of an actinic radiation stabilizer composition effective to stabilize the material against the effects of actinic radiation, wherein the actinic radiation stabilizer composition comprises a bondable triazine compound of formula (I), (II) or (III):

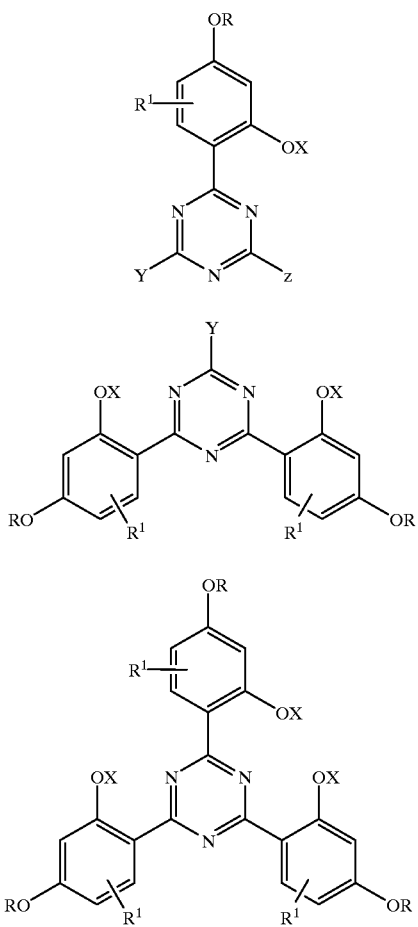

(I)

(II)

(III)

wherein
each X is independently selected from hydrogen and a blocking group; each of Y and Z is independently selected from an aryl ring of the formula (IV)

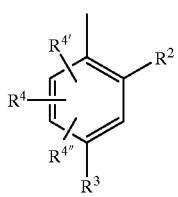

(IV)

each R is independently selected from a hydrogen, a hydrocarbyl group and a functional hydrocarbyl group;
each $R^1$, $R^2$, $R^4$, $R^{4'}$ and $R^{4''}$ is independently selected from hydrogen, hydrocarbyl, functional hydrocarbyl, —O(hydrocarbyl), —O(functional hydrocarbyl), —SR, halogen, —$SO_2R$, —$SO_3R$, —COOR, —COR, —OCOR, —NRR and cyano; and
each $R^3$ is independently selected from —R, —OR, —SR, halogen, —$SO_2R$, —$SO_3R$, —COOR, —COR, —NRR and cyano;
characterized in that at least one R group of a 4-position —OR group is selected from a group of the formulas (V), (VI) and (VII):

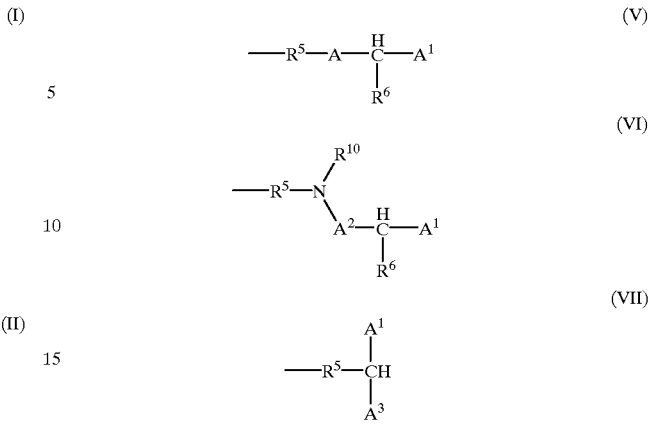

(V)

(VI)

(VII)

wherein
A is selected from —O(O)C—; —C(O)—; —SO—; —$SO_2$—; and —$OSO_2$—;
each of $A^1$ and $A^3$ is independently selected from —$COOR^7$; —$COO^-M^+$; —$C(O)R^7$; —$C(O)NR^7R^8$; —CN; —$NO_2$; —$SOR^7$; —$SO_2R^7$; —$SO_2OR^7$ and —$SO_2NR^7R^8$;
$A^2$ is selected from —C(O)—; —$R^9C(O)$—; —$R^9OC(O)$—; —SO—; $R^9SO$—; —$SO_2$; —$R^9SO_2$—; and —$R^9OSO_2$—;
$M^+$ is a cationic moiety;
each of $R^5$ and $R^9$ is independently a hydrocarbylene group;
$R^6$ is selected from H and an alkyl of 1–4 carbon atoms; and
each of $R^7$, $R^8$ and $R^{10}$ is independently selected from H, a hydrocarbyl group and a functional hydrocarbyl group,
wherein each blocking group is independently selected from at least one member of the group consisting of allyl, —$COR^a$, —$O_2R^b$, —$SiR^cR^dR^e$, —$PR^fR^g$, —$POR^fR^g$, and —$CONHR^h$;
wherein
each $R^a$ is independently selected from $C_1$–$C_8$ alkyl, halogen-substituted $C_1$–$C_8$ alkyl, $C_5$–$C_{12}$ cycloalkyl, $C_2$–$C_8$ alkenyl, —$CH_2$—CO—$CH_3$, $C_1$–$C_{12}$ alkoxy, and phenyl or phenoxy which is unsubstituted or substituted by $C_1$–$C_{12}$ alkyl, $C_1$–$C_4$ alkoxy, halogen and/or benzyl;
each $R^b$ is independently selected from $C_1$–$C_{12}$ alkyl, $C_6$–$C_{10}$ aryl and $C_7$–$C_{18}$ alkylaryl;
each $R^c$, $R^d$ and $R^e$ is independently selected from $C_1$–$C_{18}$ alkyl, cyclohexyl, phenyl and $C_1$–$C_{18}$ alkoxy;
each $R^f$ and $R^g$ is independently selected from $C_1$–$C_{12}$ alkoxy, $C_1$–$C_{12}$ alkyl, $C_5$–$C_{12}$ cycloalkyl, and phenyl or phenoxy which is unsubstituted or substituted by $C_1$–$C_{12}$ alkyl, $C_1$–$C_4$ alkoxy, halogen and/or benzyl; and
each $R^h$ is independently selected from $C_1$–$C_8$ alkyl, $C_5$–$C_{12}$ cycloalkyl, $C_2$–$C_8$ alkenyl, —$CH_2$—CO—$CH_3$, and phenyl which is unsubstituted or substituted by $C_1$–$C_{12}$ alkyl, $C_2$–$C_8$ alkenyl, $C_1$–$C_4$ alkoxy, halogen and/or benzyl; and
the triazine compound is chemically bondable to a material to be stabilized through the group of formula (V), (VI) or (VII).

2. The method of claim 1, wherein the material to be stabilized is an organic polymer and the compound is incorporated in an amount from about 0.01 to about 20% by weight based on the weight of the organic polymer.

3. The method of claim 2, wherein the compound is incorporated into the organic polymer by chemical bonding during and/or subsequent to the preparation of the organic polymer.

4. A method of protecting a substrate against degradation by actinic radiation by applying to the substrate a film containing an actinic radiation screening composition in an amount effective to reduce the amount of actinic radiation impinging on the substrate, wherein the actinic radiation screening composition comprises a bondable triazine compound of formula (I), (II) or (III):

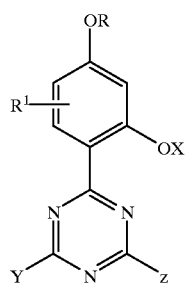

(I)

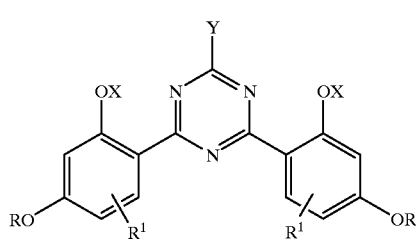

(II)

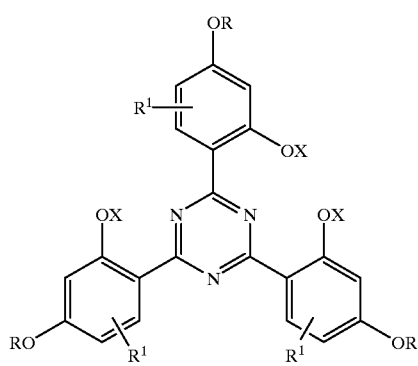

(III)

wherein each X is independently selected from hydrogen and a blocking group; each of Y and Z is independently selected from an aryl ring of the formula (IV)

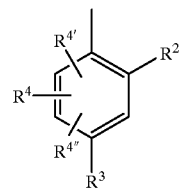

(IV)

each R is independently selected from a hydrogen, a hydrocarbyl group and a functional hydrocarbyl group;

each $R^1$, $R^2$, $R^4$, $R^{4'}$ and $R^{4''}$ is independently selected from hydrogen, hydrocarbyl, functional hydrocarbyl, —O(hydrocarbyl), —O(functional hydrocarbyl), —SR, halogen, —SO$_2$R, —SO$_3$R, —COOR, —COR, —OCOR, —NRR and cyano; and each $R^3$ is independently selected from —R, —OR, —SR, halogen, —SO$_2$R, —SO$_3$R, —COOR, —COR, —NRR and cyano;

characterized in that at least one R group of a 4-position —OR group is selected from a group of the formulas (V), (VI) and (VII):

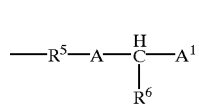

(V)

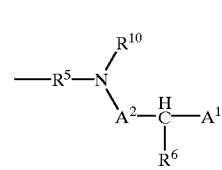

(VI)

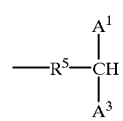

(VII)

wherein

A is selected from —O(O)C—; —C(O)—; —SO—; —SO$_2$—; and —OSO$_2$—;

each of $A^1$ and $A^3$ is independently selected from —COOR$^7$; —COO$^-$M$^+$; —C(O)R$^7$; —C(O)NR$^7$R$^8$; —CN; —NO$_2$; —SOR$^7$; —SO$_2$R$^7$; —SO$_2$R$^7$ and —SO$_2$NR$^7$R$^8$;

$A^2$ is selected from —C(O)—; —R$^9$C(O)—; —R$^9$OC(O)—; —SO—; R$^9$SO—; —SO$_2$; —R$^9$SO$_2$—; and —R$^9$OSO$_2$—;

M$^+$ is a cationic moiety;

each of $R^5$ and $R^9$ is independently a hydrocarbylene group;

$R^6$ is selected from H and an alkyl of 1–4 carbon atoms; and each of $R^7$, $R^8$ and $R_{10}$ is independently selected from H, a hydrocarbyl group and a functional hydrocarbyl group, wherein each blocking group is independently selected from at least one member of the group consisting of allyl, —COR$^a$, —O$_2$R$^b$, —SiR$^c$R$^d$R$^e$, —PR$^f$R$^g$, —POR$^f$R$^g$, and —CONHR$^h$;

wherein

- each R$^a$ is independently selected from C$_1$–C$_8$ alkyl, halogen-substituted C$_1$–C$_8$ alkyl, C$_5$–C$_{12}$ cycloalkyl, C$_2$–C$_8$ alkenyl, —CH$_2$—CO—CH$_3$, C$_1$–C$_{12}$ alkoxy, and phenyl or phenoxy which is unsubstituted or substituted by C$_1$–C$_{12}$ alkyl, C$_1$–C$_4$ alkoxy, halogen and/or benzyl;
- each R$^b$ is independently selected from C$_1$–C$_{12}$ alkyl, C$_6$–C$_{10}$ aryl and C$_7$–C$_{18}$ alkylaryl;
- each R$^c$, R$^d$ and R$^e$ is independently selected from C$_1$–C$_{18}$ alkyl, cyclohexyl, phenyl and C$_1$–C$_{18}$ alkoxy;
- each R$^f$ and R$^g$ is independently selected from C$_1$–C$_{12}$ alkoxy, C$_1$–C$_2$ alkyl, C$_5$–C$_{12}$ cycloalkyl, and phenyl or phenoxy which is unsubstituted or substituted by C$_1$–C$_{12}$ alkyl, C$_1$–C$_4$ alkoxy, halogen and/or benzyl; and
- each R$^h$ is independently selected from C$_1$–C$_8$ alkyl, C$_5$–C$_{12}$ cycloalkyl, C$_2$–C$_8$ alkenyl, —CH$_2$—CO—CH$_3$, and phenyl which is unsubstituted or substituted by C$_1$–C$_{12}$ alkyl, C$_2$–C$_8$ alkenyl, C$_1$–C$_4$alkoxy, halogen and/or benzyl; and
- the triazine compound is chemically bondable to a material to be stabilized through the group of formula (V), (VI) or (VII).

5. A coating composition suitable for forming a film stabilized against degradation by actinic radiation, comprising a film-forming binder composition and an actinic radiation stabilizing amount of a stabilizer composition, wherein the stabilizer composition comprises a bondable triazine compound of formula (I), (II) or (III):

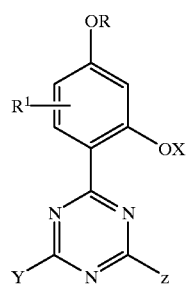

(I)

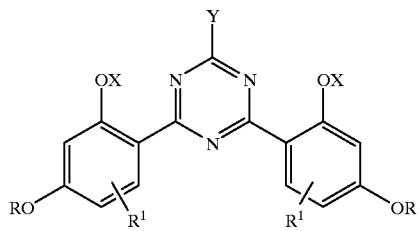

(II)

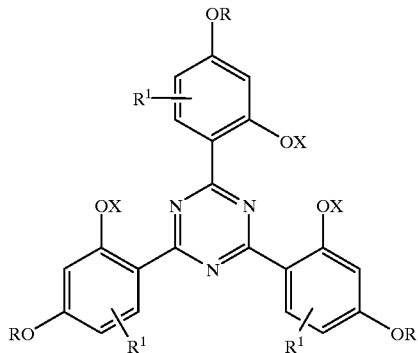

(III)

wherein
each X is independently selected from hydrogen and a blocking group; each of Y and Z is independently selected from an aryl ring of the formula (IV)

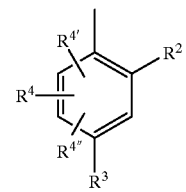

(IV)

each R is independently selected from a hydrogen, a hydrocarbyl group and a functional hydrocarbyl group;
each R$^1$, R$^2$, R$^4$, R$^{4'}$ and R$^{4''}$ is independently selected from hydrogen, hydrocarbyl, functional hydrocarbyl, —O(hydrocarbyl), —O(functional hydrocarbyl), —SR, halogen, —SO$_2$R, —SO$_3$R, —COOR, —COR, —OCOR, —NRR and cyano; and
each R$^3$ is independently selected from —R, —OR, —SR, halogen, —SO$_2$R, —SO$_3$R, —COOR, —COR, —NRR and cyano;
characterized in that at least one R group of a 4-position —OR group is selected from a group of the formulas (V), (VI) and (VII):

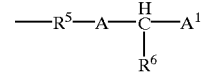

(V)

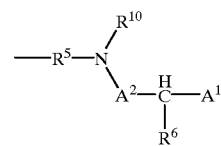

(VI)

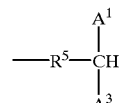

(VII)

wherein

A is selected from —O(O)C—; —C(O)—; —SO—; —SO$_2$—; and —OSO$_2$—;

each of A$^1$ and A$^3$ is independently selected from —COOR$^7$; —COO$^-$M$^+$; —C(O)R$^7$; —C(O)NR$^7$R$^8$; —CN; —NO$_2$; —SOR$^7$; —SO$_2$R$^7$; —SO$_2$OR$^7$ and —SO$_2$NR$^7$R$^8$;

A$^2$ is selected from —C(O)—; —R$^9$C(O)—; —R$^9$OC(O)—; —SO—; R$^9$SO—; —SO$_2$; —R$^9$SO$_2$—; and M$^+$ is a cationic moiety;

each of R$^5$ and R$^9$ is independently a hydrocarbylene group;

R$^6$ is selected from H and an alkyl of 1–4 carbon atoms; and each of R$^7$, R$^8$ and R$^{10}$ is independently selected from H, a hydrocarbyl group and a functional hydrocarbyl group, wherein each blocking group is independently selected from at least one member of the group consisting of allyl, —COR$^a$, —O$_2$R$^b$, —SiR$^c$R$^d$R$^e$, —PR$^f$R$^g$, —POR$^f$R$^g$, and —CONHR$^h$;

wherein each R$^a$ is independently selected from C$_1$–C$_8$ alkyl, halogen-substituted C$_1$–C$_8$ alkyl, C$_5$–C$_{12}$ cycloalkyl, C$_2$–C$_8$ alkenyl, —CH$_2$—CO—CH$_3$, C$_1$–C$_{12}$ alkoxy, and phenyl or phenoxy which is unsubstituted or substituted by C$_1$–C$_{12}$ alkyl, C$_1$–C$_4$ alkoxy, halogen and/or benzyl;

each R$^b$ is independently selected from C$_1$–C$_{12}$ alkyl, C$_6$–C$_{10}$ aryl and C$_7$–C$_{18}$ alkylaryl;

each R$^c$, R$^d$ and R$^e$ is independently selected from C$_1$–C$_{18}$ alkyl, cyclohexyl, phenyl and C$_1$–C$_{18}$ alkoxy;

each R$^f$ and R$^g$ is independently selected from C$_1$–C$_{12}$ alkoxy, C$_1$–C$_{12}$ alkyl, C$_5$–C$_{12}$ cycloalkyl, and phenyl or phenoxy which is unsubstituted or substituted by C$_1$–C$_{12}$ alkyl, C$_1$–C$_4$ alkoxy, halogen and/or benzyl; and each R$^h$ is independently selected from C$_1$–C$_{18}$ alkyl, C$_5$–C$_{12}$ cycloalkyl, C$_2$–C$_8$ alkenyl, —CH$_2$—CO—CH$_3$, and phenyl which is unsubstituted or substituted by C$_1$–C$_{12}$ alkyl, C$_2$–C$_8$ alkenyl, C$_1$–C$_4$ alkoxy, halogen and/or benzyl; and the triazine compound is chemically bondable to a material to be stabilized through the group of formula (V), (VI) or (VII).

6. The coating composition of claim 5, wherein the film-forming binder is reactive with the compound under cure conditions.

7. A stabilized crosslinked film prepared by curing the coating composition of claim 6.

8. The coating composition of claim 7, wherein the stabilizer composition further comprises a monomeric hindered amine light stabilizer.

9. The coating composition of claim 7, wherein the stabilizer composition further comprises an ultraviolet light absorber.

10. The coating composition of claim 9, wherein the ultraviolet light absorber is a benzotriazole or 2-(2-hydroxyphenyl)-1,3,5-triazine.

* * * * *